United States Patent
Tweedle et al.

(10) Patent No.: US 12,370,273 B2
(45) Date of Patent: Jul. 29, 2025

(54) 3E8.SCFV.CYS-IR800 CONJUGATE TARGETING TAG-72 IN AN ORTHOTOPIC COLORECTAL CANCER MODEL

(71) Applicant: OHIO STATE INNOVATION FOUNDATION, Columbus, OH (US)

(72) Inventors: Michael F. Tweedle, Bexley, OH (US); Li Gong, Columbus, OH (US)

(73) Assignee: Ohio Sate Innovation Foundation, Columbus, OH (US)

( * ) Notice: Subject to any disclaimer, the term of this patent is extended or adjusted under 35 U.S.C. 154(b) by 0 days.

(21) Appl. No.: 18/524,613

(22) Filed: Nov. 30, 2023

(65) Prior Publication Data

US 2024/0108764 A1    Apr. 4, 2024

Related U.S. Application Data

(62) Division of application No. 16/270,548, filed on Feb. 7, 2019, now abandoned.

(60) Provisional application No. 62/627,495, filed on Feb. 7, 2018.

(51) Int. Cl.
*G01N 31/00* (2006.01)
*A61K 9/00* (2006.01)
*A61K 51/04* (2006.01)
*C07K 16/30* (2006.01)
*G01N 33/53* (2006.01)

(52) U.S. Cl.
CPC ........ *A61K 51/0459* (2013.01); *A61K 9/0019* (2013.01); *C07K 16/30* (2013.01)

(58) Field of Classification Search
USPC ............. 435/7.1, 7.21, 283.1; 436/501, 518; 424/9.1, 130.1, 520; 422/430; 530/300, 530/350
See application file for complete search history.

(56) References Cited

U.S. PATENT DOCUMENTS

| | | | |
|---|---|---|---|
| 10,758,632 B2 * | 9/2020 | Yazaki | C07K 16/3007 |
| 2016/0176979 A1 * | 6/2016 | Magliery | C07K 16/3092 424/1.49 |

OTHER PUBLICATIONS

Gong et al. (Mol. Imaging Biol. 2018, 20:47-54, published online Jun. 22, 2017). (Year: 2017).*
Adumeau P, Sharma SK, Brent C, Zeglis BM. Site-Specifically Labeled Immunoconjugates for Molecular Imaging-Part 1: Cysteine Residues and Glycans. Mol Imaging Biol. 2016;18(1):1-17.
Adumeau P, Sharma SK, Brent C, Zeglis BM. Site-Specifically Labeled Immunoconjugates for Molecular Imaging-Part 2: Peptide Tags and Unnatural Amino Acids. Mol Imaging Biol. 2016;18(2):153-65.
Antoniou SA, Antoniou GA, Koch OO, Pointner R, Granderath FA. Robot-assisted laparoscopic surgery of the colon and rectum. Surg Endosc. 2012;26(1):1-11.
Boonstra MC, van Driel PBAA, van Willigen DM, Stammes MA, Prevoo HAJM, Tummers QRJG, et al. uPAR-targeted multimodal tracer for pre- and intraoperative imaging in cancer surgery. Oncotarget. 2015;6(16):14260-73.
Boonstra MC, Verspaget HW, Ganesh S, Kubben FJGM, Vahrmeijer AL, de Velde CJHV, et al. Clinical Applications of the Urokinase Receptor (uPAR) for Cancer Patients. Curr Pharm Des. 2011;17(19):1890-910.
Ding HM, Carlton MM, Povoski SP, Milum K, Kumar K, Kothandaraman S, et al. Site Specific Discrete PEGylation of I-124-Labeled mCC49 Fab' Fragments Improves Tumor MicroPET/CT Imaging in Mice. Bioconjug Chem. 2013;24(11):1945-54.
Frangioni JV. In vivo near-infrared fluorescence imaging. Curr Opin Chem Biol. 2003;7(5):626-34.
Fu XY, Besterman JM, Monosov A, Hoffman RM. Models of human metastatic colon cancer in nude mice orthotopically constructed by using histologically intact patient specimens. Proc Natl Acad Sci U S A. 1991;88(20):9345-9.
Hermanson GT. Discrete PEG Reagents. Bioconjugate Techniques, 2nd edition. 2nd Edition ed. USA: Elsevier; 2008. p. 732-3.
Hiroshima Y, Maawy A, Metildi CA, Zhang Y, Uehara F, Miwa S, et al. Successful Fluorescence-Guided Surgery on Human Colon Cancer Patient-Derived Orthotopic Xenograft Mouse Models Using a Fluorophore-Conjugated Anti-CEA Antibody and a Portable Imaging System. Journal of Laparoendoscopic & Advanced Surgical Techniques. 2014;24(4):241-7.
Horton KM, Abrams RA, Fishman EK. Spiral CT of colon cancer: Imaging features and role in management. Radiographics. 2000;20(2):419-30.
Johnson VG, Schlom J, Paterson AJ, Bennett J, Magnani JL, Colcher D. Analysis of a human tumor-associated glycoprotein (TAG-72) identified by monoclonal antibody B72.3. Cancer Res. 1986;46(2):850-7.
Kinkel K, Lu Y, Both M, Warren RS, Thoeni RF. Detection of hepatic metastases from cancers of the gastrointestinal tract by using noninvasive imaging methods (US, CT, MR imaging, PET): A meta-analysis. Radiology. 2002;224(3):748-56.
Koppe MJ, Soede AC, Pels W, Oyen WJ, Goldenberg DM, Bleichrodt RP, et al. Experimental radioimmunotherapy of small peritoneal metastases of colorectal origin. Int J Cancer. 2003;106(6):965-72.
Kosaka N, Ogawa M, Choyke PL, Kobayashi H. Clinical implications of near-infrared fluorescence imaging in cancer. Future Oncology. 2009;5(9):1501-11.
Kuhry E, Schwenk W, Gaupset R, Romild U, Bonjer J. Long-term outcome of laparoscopic surgery for colorectal cancer: a cochrane systematic review of randomised controlled trials. Cancer Treat Rev. 2008;34(6):498-504.
Loy TS, Nashelsky MB. Reactivity of B72.3 with adenocarcinomas. An immunohistochemical study of 476 cases. Cancer. 1993;72(8):2495-8.
Maawy AA, Hiroshima Y, Zhang Y, Luiken GA, Hoffman RM, Bouvet M. Polyethylene Glycol (PEG) Linked to Near Infrared (NIR) Dyes Conjugated to Chimeric Anti-Carcinoembryonic Antigen (CEA) Antibody Enhances Imaging of Liver Metastases in a Nude-Mouse Model of Human Colon Cancer. PLoS One. 2014;9(5).

(Continued)

*Primary Examiner* — Lisa V Cook
(74) *Attorney, Agent, or Firm* — Meunier Carlin & Curfman LLC

(57) ABSTRACT

Disclosed are anti-TAG-72 imaging agents and methods of their use.

5 Claims, 12 Drawing Sheets

Specification includes a Sequence Listing.

(56) References Cited

OTHER PUBLICATIONS

Mori A, Arii S, Furutani M, Mizumoto M, Uchida S, Furuyama H, et al. Soluble Flt-1 gene therapy for peritoneal metastases using HVJ-cationic liposomes. Gene Ther. 2000;7(12):1027-33.

Nayak TK, Garmestani K, Milenic DE, Brechbiel MW. PET and MRI of metastatic peritoneal and pulmonary colorectal cancer in mice with human epidermal growth factor receptor 1-targeted 89Zr-labeled panitumumab. J Nucl Med. 2012;53(1):113-20.

Park JY, Murakami T, Lee JY, Zhang Y, Hoffman RM, Bouvet M. Fluorescent-Antibody Targeting of Insulin-Like Growth Factor-1 Receptor Visualizes Metastatic Human Colon Cancer in Orthotopic Mouse Models. PLoS One. 2016;11(1).

Povoski SP, Hatzaras IS, Mojzisik CM, Arnold MW, Hinkle GH, Hitchcock CL, et al. Antigen-directed cancer surgery for primary colorectal cancer: 15-year survival analysis. Ann Surg Oncol. 2012; 19(1):131-8.

Povoski SP, Neff RL, Mojzisik CM, O'Malley DM, Hinkle GH, Hall NC, et al. A comprehensive overview of radioguided surgery using gamma detection probe technology. World J Surg Oncol. 2009;7:11, 63 pages.

Reza MM, Blasco JA, Andradas E, Cantero R, Mayol J. Systematic review of laparoscopic versus open surgery for colorectal cancer. Br J Surg. 2006;93(8):921-8.

Rijpkema M, Oyen WJ, Bos D, Franssen GM, Goldenberg DM, Boerman OC. SPECT- and Fluorescence Image-Guided Surgery Using a Dual-Labeled Carcinoembryonic Antigen-Targeting Antibody. J Nucl Med. 2014;55(9):1519-24.

Rogers BE, Roberson PL, Shen S, Khazaeli MB, Carpenter M, Yokoyama S, et al. Intraperitoneal radioimmunotherapy with a humanized anti-TAG-72 (CC49) antibody with a deleted CH2 region. Cancer Biother Radiopharm. 2005;20(5):502-13.

Rosenthal EL, Warram JM, de Boer E, Basilion JP, Biel MA, Bogyo M, et al. Successful Translation of Fluorescence Navigation During Oncologic Surgery: A Consensus Report. J Nucl Med. 2016;57(1):144-50.

Rowe DE, Carroll RJ, Day CL. Prognostic factors for local recurrence, metastasis, and survival rates in squamous-cell carcinoma of the skin, ear, and lip—implications for treatment modality selection. J Am Acad Dermatol. 1992;26(6):976-90.

Ryu JH, Na JH, Ko HK, You DG, Park S, Jun E, et al. Non-invasive optical imaging of cathepsin B with activatable fluorogenic nanoprobes in various metastatic models. Biomaterials. 2014;35(7):2302-11.

Schaafsma BE, Mieog JSD, Hutteman M, Van der Vorst JR, Kuppen PJK, Lowik CWGM, et al. The Clinical Use of Indocyanine Green as a Near-Infrared Fluorescent Contrast Agent for Image-Guided Oncologic Surgery. J Surg Oncol. 2011;104(3):323-32.

Sevick-Muraca EM. Translation of near-infrared fluorescence imaging technologies: emerging clinical applications. Annu Rev Med. 2012;63:217-31.

Sheer DG, Schlom J, Cooper HL. Purification and composition of the human tumor-associated glycoprotein (TAG-72) defined by monoclonal antibodies CC49 and B72.3. Cancer Res. 1988;48(23):6811-8.

Slavin-Chiorini DC, Horan Hand PH, Kashmiri SV, Calvo B, Zaremba S, Schlom J. Biologic properties of a CH2 domain-deleted recombinant immunoglobulin. Int J Cancer. 1993;53(1):97-103.

Stewart SL, Wike JM, Kato I, Lewis DR, Michaud F. A population-based study of colorectal cancer histology in the United States, 1998-2001. Cancer. 2006;107(5 Suppl):1128-41.

Sun D, Bloomston M, Hinkle G, Al-Saif OH, Hall NC, Povoski SP, et al. Radioimmunoguided surgery (RIGS), PET/CT image-guided surgery, and fluorescence image-guided surgery: past, present, and future. Journal of surgical oncology. 2007;96(4):297-308.

Van Dam GM, Themelis G, Crane LM, Harlaar NJ, Pleijhuis RG, Kelder W, et al. Intraoperative tumor-specific fluorescence imaging in ovarian cancer by folate receptor-alpha targeting: first in-human results. Nat Med. 2011;17(10):1315-9.

Yanagihara K, Takigahira M, Tanaka H, Komatsu T, Fukumoto H, Koizumi F, et al. Development and biological analysis of peritoneal metastasis mouse models for human scirrhous stomach cancer. Cancer Sci. 2005;96(6):323-32.

Yoon SO, Lee TS, Kim SJ, Jang MH, Kang YJ, Park JH, et al. Construction, affinity maturation, and biological characterization of an anti-tumor-associated glycoprotein-72 humanized antibody. J Biol Chem. 2006;281(11):6985-92.

Zou P, Povoski SP, Hall NC, Carlton MM, Hinkle GH, Xu RX, et al. I-124-HuCC49deltaC(H)2 for TAG-72 antigen-directed positron emission tomography (PET) imaging of LS174T colon adenocarcinoma tumor implants in xenograft mice: preliminary results. World J Surg Oncol. 2010;8.

Zou P, Xu S, Povoski SP, Wang A, Johnson MA, Martin EW, Jr., et al. Near-infrared fluorescence labeled anti-TAG-72 monoclonal antibodies for tumor imaging in colorectal cancer xenograft mice. Mol Pharm. 2009;6(2):428-40.

\* cited by examiner

```
                          SEQUENCE LISTING

Sequence total quantity: 11
SEQ ID NO: 1            moltype = AA   length = 298
FEATURE                 Location/Qualifiers
REGION                  1..298
                        note = Synthesized
source                  1..298
                        mol_type = protein
                        organism = synthetic construct
SEQUENCE: 1
MKYLLPTAAA GLLLLAAQPA MAAHHHHHHG SSGGGENLYF QGSSGDIVMT QSPDSLAVSL    60
GERATINCKS SQSVLYSSNN KNYLAWYQQK PGQPPKLLIY WASTRESGVP DRFSGSGSGT   120
DFTLTISSLQ AEDVAVYYCQ QYYSYPLTFG GTKVEIKLS ADDAKKDAAK KDDAKKDDAK   180
KDLQVQLVQS GAEVKKPGAS VKVSCKASGY TFTDHAIHWV RQAPGQRLEW MGYFSPGNDD   240
FKYSQKFQGR VTITADKSAS TAYMELSSLR SEDTAVYYCA RSWIMQYWGQ GTLVTVSS    298

SEQ ID NO: 2            moltype = AA   length = 299
FEATURE                 Location/Qualifiers
REGION                  1..299
                        note = Synthesized
source                  1..299
                        mol_type = protein
                        organism = synthetic construct
SEQUENCE: 2
MKYLLPTAAA GLLLLAAQPA MAAHHHHHHG SSGGGENLYF QGSSGDIVMT QSPDSLAVSL    60
GERATINCKS SQSVLYSSNN KNYLAWYQQK PGQPPKLLIY WASTRESGVP DRFSGSGSGT   120
DFTLTISSLQ AEDVAVYYCQ QYYSYPLTFG GTKVEIKLS ADDAKKDAAK KDDAKKDDAK   180
KDLQVQLVQS GAEVKKPGAS VKVSCKASGY TFTDHAIHWV RQAPGQRLEW MGYFSPGNDD   240
FKYSQKFQGR VTITADKSAS TAYMELSSLR SEDTAVYYCA RSWIMQYWGQ GTLVTVSSC   299

SEQ ID NO: 3            moltype = AA   length = 22
FEATURE                 Location/Qualifiers
REGION                  1..22
                        note = Synthesized
source                  1..22
                        mol_type = protein
                        organism = synthetic construct
SEQUENCE: 3
MKYLLPTAAA GLLLLAAQPA MA                                            22
```

```
SEQ ID NO: 4            moltype = AA    length = 19
FEATURE                 Location/Qualifiers
REGION                  1..19
                        note = Synthesized
source                  1..19
                        mol_type = protein
                        organism = synthetic construct
SEQUENCE: 4
AHHHHHHGSS GGGENLYFQ                                                    19

SEQ ID NO: 5            moltype = AA    length = 4
FEATURE                 Location/Qualifiers
REGION                  1..4
                        note = Synthesized
source                  1..4
                        mol_type = protein
                        organism = synthetic construct
SEQUENCE: 5
GSSG                                                                    4

SEQ ID NO: 6            moltype = AA    length = 25
FEATURE                 Location/Qualifiers
REGION                  1..25
                        note = Synthesized
source                  1..25
                        mol_type = protein
                        organism = synthetic construct
SEQUENCE: 6
LSADDAKKDA AKKDDAKKDD AKKDL                                             25

SEQ ID NO: 7            moltype = DNA    length = 906
FEATURE                 Location/Qualifiers
misc_feature            1..906
                        note = Synthesized
source                  1..906
                        mol_type = other DNA
                        organism = synthetic construct
SEQUENCE: 7
catatgaaat atctgttacc tactgctgct gcgggcctgc tattattagc ggcacaacca        60
gcaatggcgg cgcatcatca tcatcatcat gggtcctcgg gcgtggcga aaatctgtat       120
tttcaggta gcagcggcga tattgtgatg acccagagcc cggatagttt ggccgttagc       180
ctgggcgaac gtgcgacgat taattgcaag agcagccaga gcgtgcttta cagcagcaac      240
aataagaatt acctggcgtg gtatcagcaa aaacccggcc agccgccgaa acttttgatt      300
tattgggcga gcacccgtga aagcggcgtg ccggatcgtt tctcgggctc aggcagcggg      360
accgatttta cgctgaccat cagcagcctt caggcggagg atgtcgcggt gtactactgc      420
cagcagtatt acagctatcc gttgaccttt ggggaaggca ccaaagtgga gatcaaactg      480
agcgcggatg atgctaagaa agatgcggcg aagaaggacg atgcgaaaaa agacgacgca      540
aaaaaggatc tgcaggtgca gctggtgcag tcgggtgcgg aagtgaagaa acctggggcg      600
tcggtgaaag tgagctgcaa agcgagcggc tatacccttta ccgatcatgc gattcattgg      660
gtgcgtcaag cgccaggcca gcgtctggaa tggatgggct atttttcccc aggcaacgat      720
gatttcaagt attcccagaa gttccaaggg cgcgtgacca ttaccgccga taaaagcgca      780
agcaccgcgt atatggagct gtccagcctg cgtagcgaag atacagcggt ttactattgc      840
gcacggagct ggattatgca atactggggc cagggcaccc tggtgaccgt gagcagctaa      900
ggatcc                                                                 906

SEQ ID NO: 8            moltype = DNA    length = 909
FEATURE                 Location/Qualifiers
misc_feature            1..909
                        note = Synthesized
source                  1..909
                        mol_type = other DNA
                        organism = synthetic construct
SEQUENCE: 8
catatgaaat atctgttacc tactgctgct gcgggcctgc tattattagc ggcacaacca        60
gcaatggcgg cgcatcatca tcatcatcat gggtcctcgg gcgtggcga aaatctgtat       120
tttcaggta gcagcggcga tattgtgatg acccagagcc cggatagttt ggccgttagc       180
ctgggcgaac gtgcgacgat taattgcaag agcagccaga gcgtgcttta cagcagcaac      240
aataagaatt acctggcgtg gtatcagcaa aaacccggcc agccgccgaa acttttgatt      300
tattgggcga gcacccgtga aagcggcgtg ccggatcgtt tctcgggctc aggcagcggg      360
accgatttta cgctgaccat cagcagcctt caggcggagg atgtcgcggt gtactactgc      420
cagcagtatt acagctatcc gttgaccttt ggggaaggca ccaaagtgga gatcaaactg      480
agcgcggatg atgctaagaa agatgcggcg aagaaggacg atgcgaaaaa agacgacgca      540
aaaaaggatc tgcaggtgca gctggtgcag tcgggtgcgg aagtgaagaa acctggggcg      600
tcggtgaaag tgagctgcaa agcgagcggc tatacccttta ccgatcatgc gattcattgg      660
gtgcgtcaag cgccaggcca gcgtctggaa tggatgggct atttttcccc aggcaacgat      720
gatttcaagt attcccagaa gttccaaggg cgcgtgacca ttaccgccga taaaagcgca      780
agcaccgcgt atatggagct gtccagcctg cgtagcgaag atacagcggt ttactattgc      840
gcacggagct ggattatgca atactggggc cagggcaccc tggtgaccgt gagcagctgt      900
```

```
taaggatcc                                                                909

SEQ ID NO: 9            moltype = AA  length = 48
FEATURE                 Location/Qualifiers
REGION                  1..48
                        note = Synthesized
source                  1..48
                        mol_type = protein
                        organism = synthetic construct
SEQUENCE: 9
MKYLLPTAAA GLLLLAAQPA MAAHHHHHHG SSGGGENLYF QGSSGDIV                      48

SEQ ID NO: 10           moltype = AA  length = 115
FEATURE                 Location/Qualifiers
REGION                  1..115
                        note = Synthesized
source                  1..115
                        mol_type = protein
                        organism = synthetic construct
SEQUENCE: 10
QVQLVQSGAE VKKPGASVKV SCKASGYTFT DHAIHWVRQA PGQRLEWMGY FSPGNDDFKY          60
SQKFQGRVTI TADKSSSTAY MELSSLRSED TAVYYCARSW IMQYWGQGTL VTVSS              115

SEQ ID NO: 11           moltype = AA  length = 113
FEATURE                 Location/Qualifiers
REGION                  1..113
                        note = Synthesized
source                  1..113
                        mol_type = protein
                        organism = synthetic construct
SEQUENCE: 11
DIVMTQSPDS LAVSLGERAT INCKSSQSVL YSSNNKNYLA WYQQKPGQPP KLLIYWASTR          60
ESGVPDRFSG SGSGTDFTLT ISSLQAEDVA VYYCQQYYSY PLTFGGGTKV EIK                113
```

3E8.SCFV.CYS-IR800 CONJUGATE TARGETING TAG-72 IN AN ORTHOTOPIC COLORECTAL CANCER MODEL

CROSS-REFERENCE TO RELATED APPLICATIONS

This application is a divisional of U.S. application Ser. No. 16/270,548 filed on Feb. 7, 2019, now abandoned, which claims benefit of U.S. Provisional Application No. 62/627,495 filed Feb. 7, 2018, applications which are incorporated herein by reference in their entirety.

SEQUENCE LISTING

A Sequence Listing conforming to the rules of WIPO Standard ST.26 is hereby incorporated by reference. Said Sequence Listing has been filed as an electronic document via PatentCenter in ASCII format encoded as XML. The electronic document, created on Nov. 29, 2023, is entitled "10336-465US2.xml", and is 17,158 bytes in size.

STATEMENT REGARDING FEDERALLY SPONSORED RESEARCH

This invention was made with Government Support under Grant Nos. P30 CA016058 and R01 EB022134 awarded by the National Institutes of Health. The Government has certain rights in the invention.

I. BACKGROUND

More than 135,000 colorectal carcinomas are predicted in 2017 (USA), 96% of which will be adenocarcinoma. The overall management of these patients, whether for early stage or more advanced disease, involves surgery within the treatment plan. It is well known that incomplete surgical clearance of the tumor and inability to locate and completely resect regional and distant metastatic disease leads to disease recurrence and poor long-term survival. Despite advances in surgery, including minimally-invasive, laparoscopic, and robotic approaches, and advances in diagnostic imaging (CT, SPECT/PET/CT, MRI, Ultrasound), surgeons still rely heavily on visual inspection and palpation that can miss occult sites of disease, especially when these sites are not apparent on preoperative external imaging (CT, US, MRI, PET and SPECT). Hence, intraoperative guidance in general has a well-established utility.

Existing external imaging technologies are, however, poorly qualified for intraoperative use, by being either not cancer specific (MRI, US, CT) or in the single case an imaging method that is cancer specific, (PET/CT or SPECT/CT), not useful in real-time because images require 15 minutes to one hour for each image to be acquired. Intraoperative frozen section analysis (FSA) by microscopy is examination of a tiny biopsy specimen collected from the surgical field from tissues suspected to harbor cancer cells during the surgery, but it also is too slow and it also evaluates only a microscopic fraction of the entire specimen collected, which in turn is only a fraction of the whole tissue. Radioguided antigen-directed surgery (RADS) uses systemically delivered radiolabeled cancer-specific antibodies (Ab) that are administered before the surgery, localize at the cancer cells, and then detectable intraoperatively with handheld radiation detection probes. This technique produced evidence of the usefulness of intraoperative detection of tumor in addition to the surgeons' vision and palpation. But the technique requires many individual measurements monitoring only 1 cm of tissue at each measurement, including a control measurement at each point back and forth to normal and suspect tissues and moving across the surgical field manually. RADS is again thus too slow (~1 minute for each 2-3 cm) for general use in colorectal patients except in rare cases where only very small areas (~10×10 cm) are to be resected. Most patients have far wider fields of surgery, across the entire abdomen including the whole liver. What is needed are new imaging techniques that do not suffer the limitations of external imaging technologies and new imaging agents for use in said methods.

II. SUMMARY

Disclosed are methods and compositions related to anti-TAG-72 imaging agents.

In one aspect, disclosed herein are anti-TAG-72 imaging agents comprising the formula Y-R, wherein Y comprises an anti-TAG-72 binding moiety and R comprises a first detectable label; wherein the first detectable label comprises any dicyanine dye (such as, for example IRdye800. AlexaFluor 790, ZW-800 (Frangioni et al), Indocyanine Green, and SO456) that emits fluorescent light that is detectable on a clinical optical NIRF imager at primarily above 800 nm.

Also disclosed herein are anti-TAG-72 imaging agents of any preceding aspect, wherein the anti-TAG-72 binding moiety is comprises an antibody or TAG-72 binding antibody fragment (such as, for example, an scFv. F(ab')2, or Fab' that binds TAG-72). For example, the anti-TAG-72 binding moiety comprises 3E8.scFv (such as, for example, as set forth in SEQ ID NO: 1).

In one aspect, disclosed herein are anti-TAG-72 imaging agents of any preceding aspect, wherein the 3E8.scFv has been modified to further comprise a terminal cysteine residue (3E8.scFv.Cys) (such as, for example, as set forth in SEQ ID NO: 2).

Also disclosed herein are anti-TAG-72 imaging agents of any preceding aspect, wherein the anti-TAG-72 imaging agent further comprises a second detectable label, such as, for example a radiolabel.

In one aspect, disclosed herein are methods of performing optical surgical navigation comprising administering to a subject the anti-TAG-72 imaging agent of any preceding aspect, wherein the anti-TAG-72 imaging agent is used as an optical surgical navigation (OSN) agent administered intraparetoneally or intravenously.

Also disclosed herein are methods of performing surgical removal of a tumor in a subject comprising administering to a subject the anti-TAG-72 imaging agent of any preceding aspect; and guiding the surgical removal of the tumor using optical surgical navigation. In some aspect, the method further comprises assaying the tumor using the anti-TAG-72 imaging agent to determine the possibility of surgical removal after administration and prior to tumor removal using optical surgical navigation. Additionally, in some aspects, disclosed herein are methods of performing surgical removal of a tumor in a subject of any preceding aspect further comprising monitoring the progress of the surgical removal.

In one aspect, disclosed herein are methods of making ®-anti-TAG-72 imaging agent comprising the formula Y-R of any preceding aspect, wherein Y comprises an anti-TAG-72 binding moiety and R comprises a first detectable label; wherein ® is a radioactive labeling atom that is useful for SPECT/CT or PET/CT, a radioactive labeling atom that is useful for RADS surgical guidance, or a radiolabeling atom useful for both SPECT/CT or PET/CT and RADS said method comprising providing an anti-TAG-72 imaging agent comprising a tyrosine residue; and reacting the biomolecule with a chloramine and an iodine source under conditions effective to form an iodinated biomolecule, wherein the iodinated biomolecule comprises an iodinated tyrosine residue.

III. BRIEF DESCRIPTION OF THE DRAWINGS

The accompanying drawings, which are incorporated in and constitute a part of this specification, illustrate several embodiments and together with the description illustrate the disclosed compositions and methods.

Figure 3:
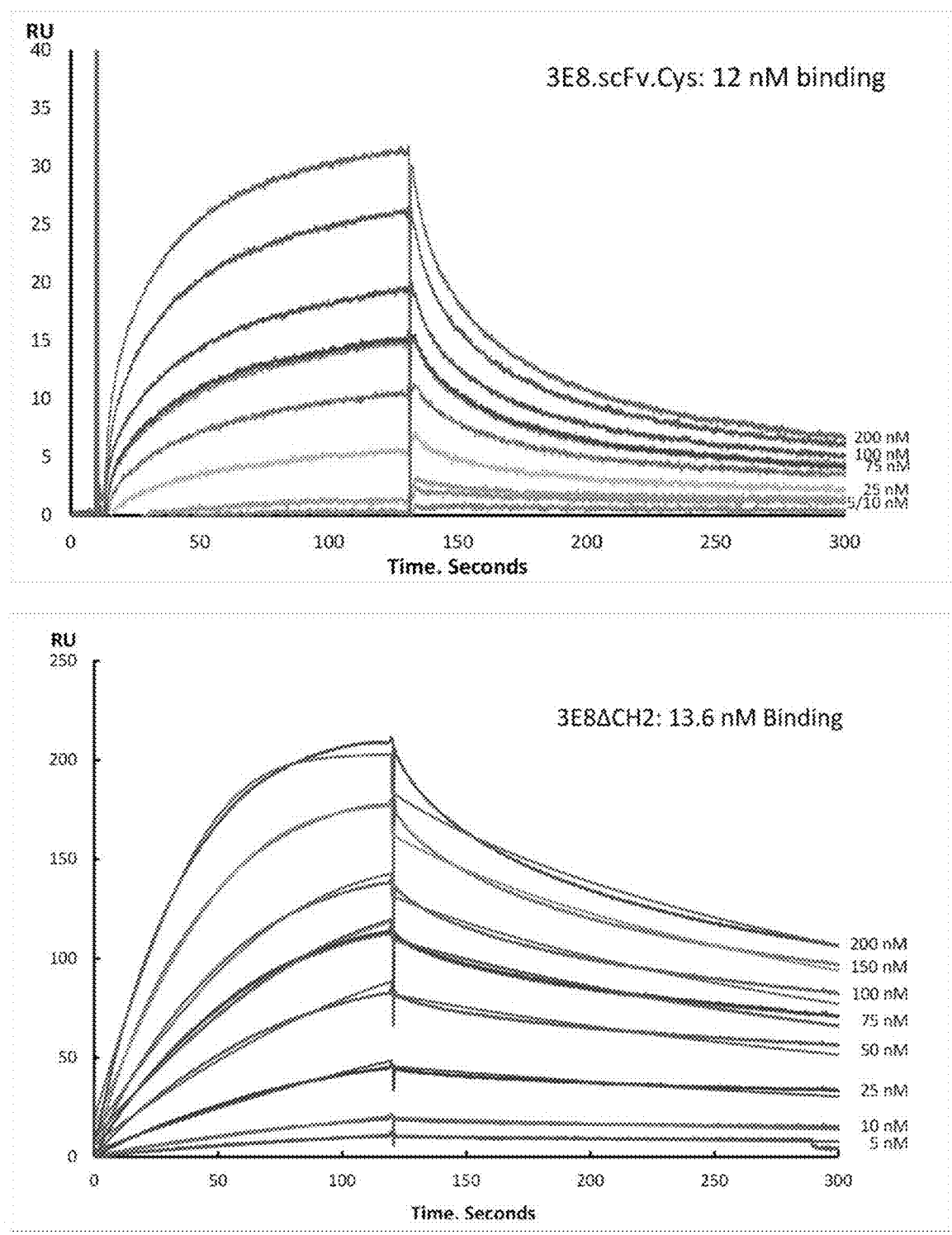

FIG. 3 shows SPR (surface plasmon resonance) traces (sensograms) for 3E8.scFv.Cys and 3E8ΔCH2 on a BSM coated surface. The technique is an established method for label-free, optically based detection of biomolecular interactions. The target ligand is coated to the dextran surface in a reaction cell, and binder protein is passed over the surface. After an association time, a solution free of binder protein is passed over the surface. Detected signals are reported as RU (response units). Rate constants are calculated from the RU vs Time curves. The quotient of the "off surface" and "on surface" rate constants is the Kd. All right side curves are "off surface", all left side of curves are "on surface."

Figure 4:
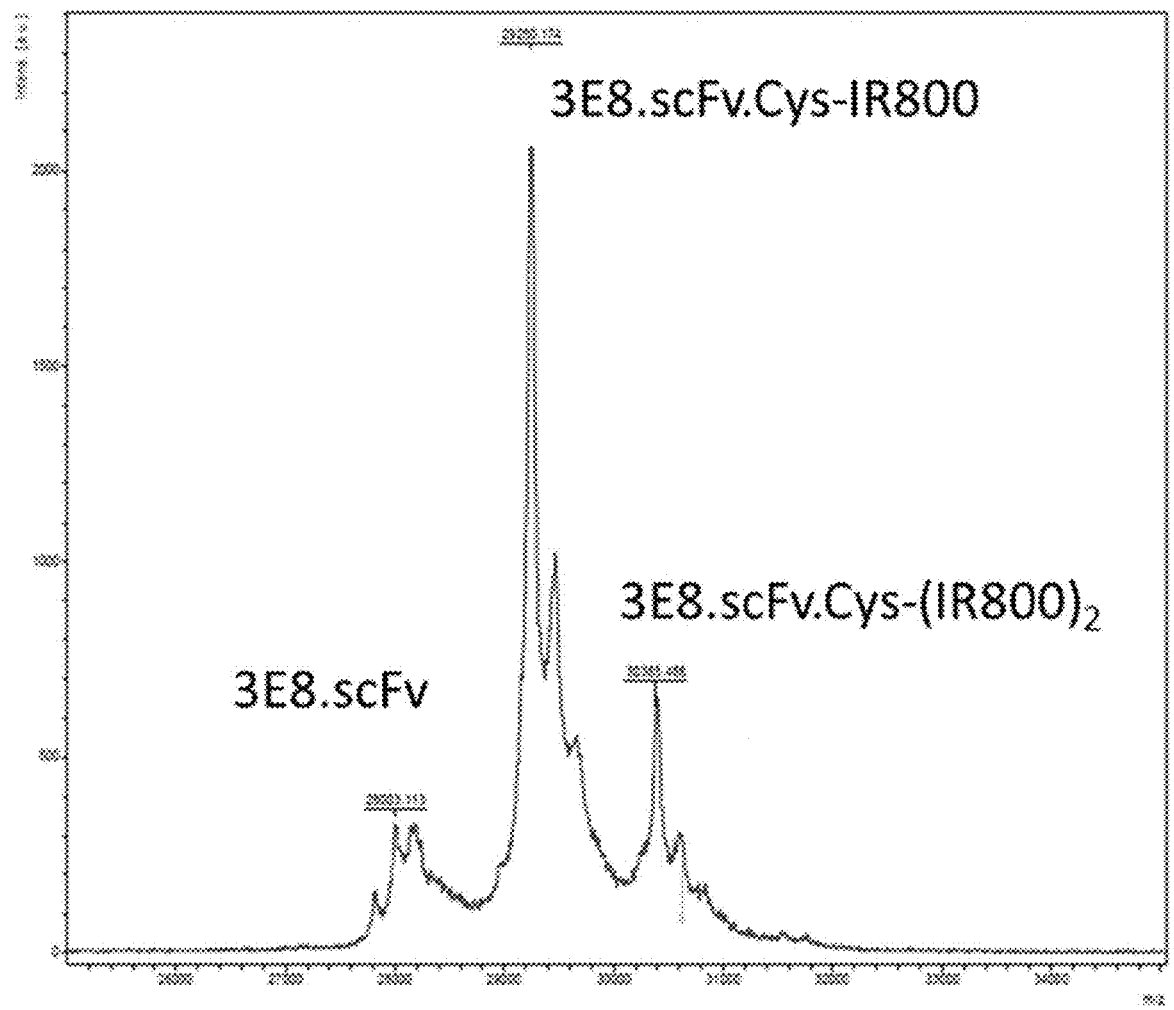

FIG. 4 shows verification of 3E8.scFv.Cys-IR800 identity by MALDI-TOF/TOF mass spectrometry. The predominant peak is at the correct mass for the protein conjugated to a single dye. The spectrum demonstrates the identity of the 1 dye:1 protein as highly predominant, hence a site-specific labeling of 3E8.scFv.Cys with IR-800-maleimide.

Figure 5:
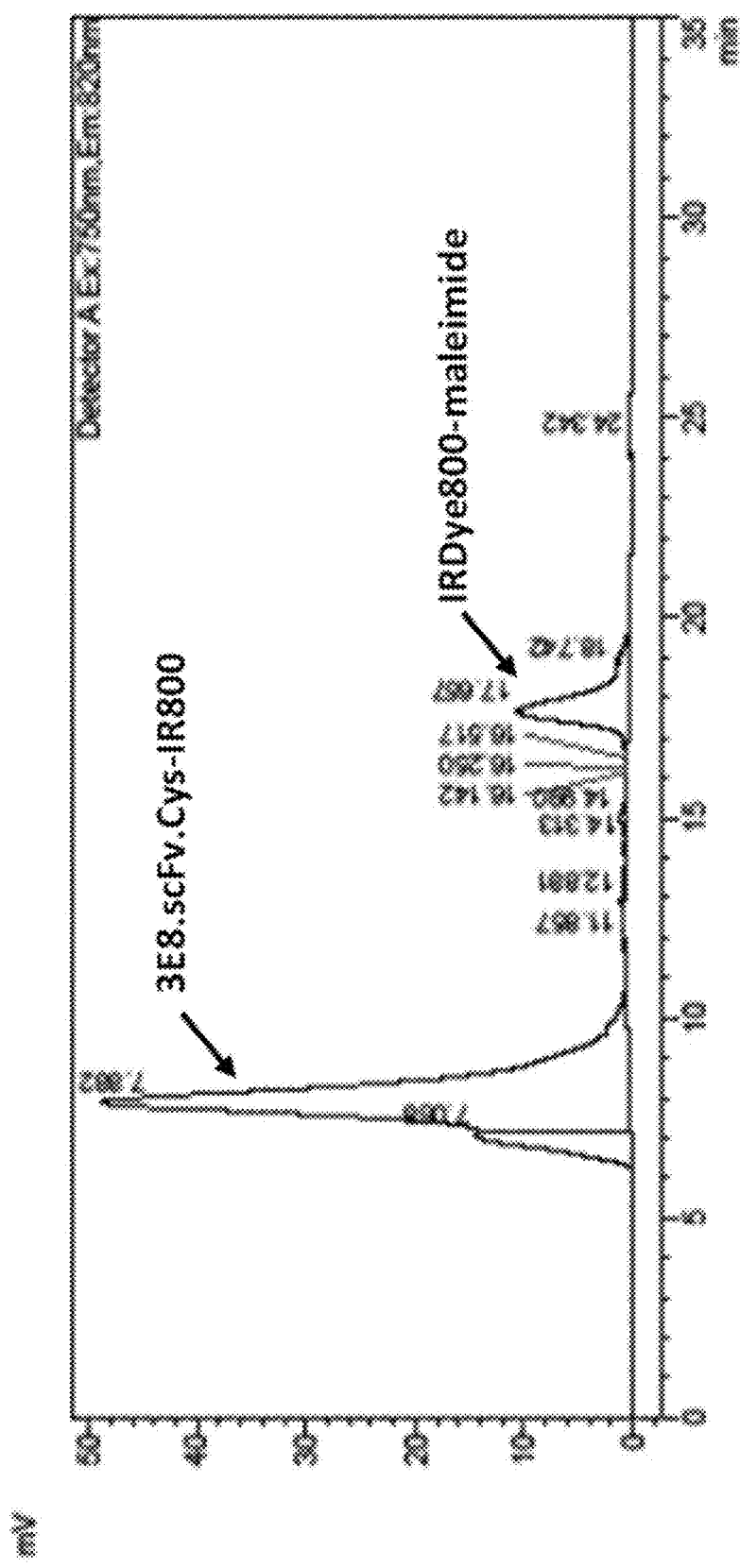

FIG. 5 shows a greater than 90% purity of 3E8.scFv.Cys-IR800 was achieved, as determined by size exclusion column HPLC with 800 nm fluorescence detection. Emission of the 3E8.scFv.Cys-IR800 is 39% less intense per mole than that of the unreacted IR800-maleimide impurity.

Figure 6:
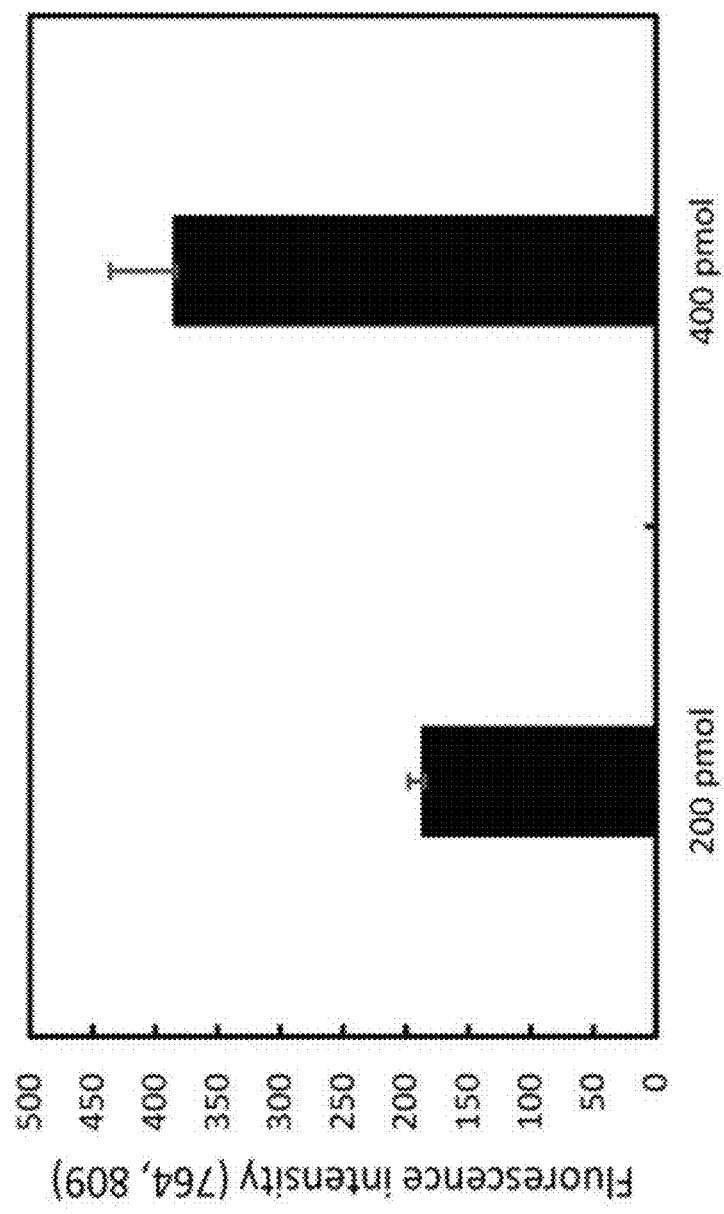

FIG. 6 shows 3E8.scFv.Cys-IR800 binding onto a human TAG-72 coated plate at two amounts in equal 100 ul volumes, detected by NIRF signal above 800 nm remaining after washing. The method was the same as was used in the LS174-T cell binding experiment in FIG. 2. The binding shows dose dependence of the concentration in the incubation media.

Figure 7:
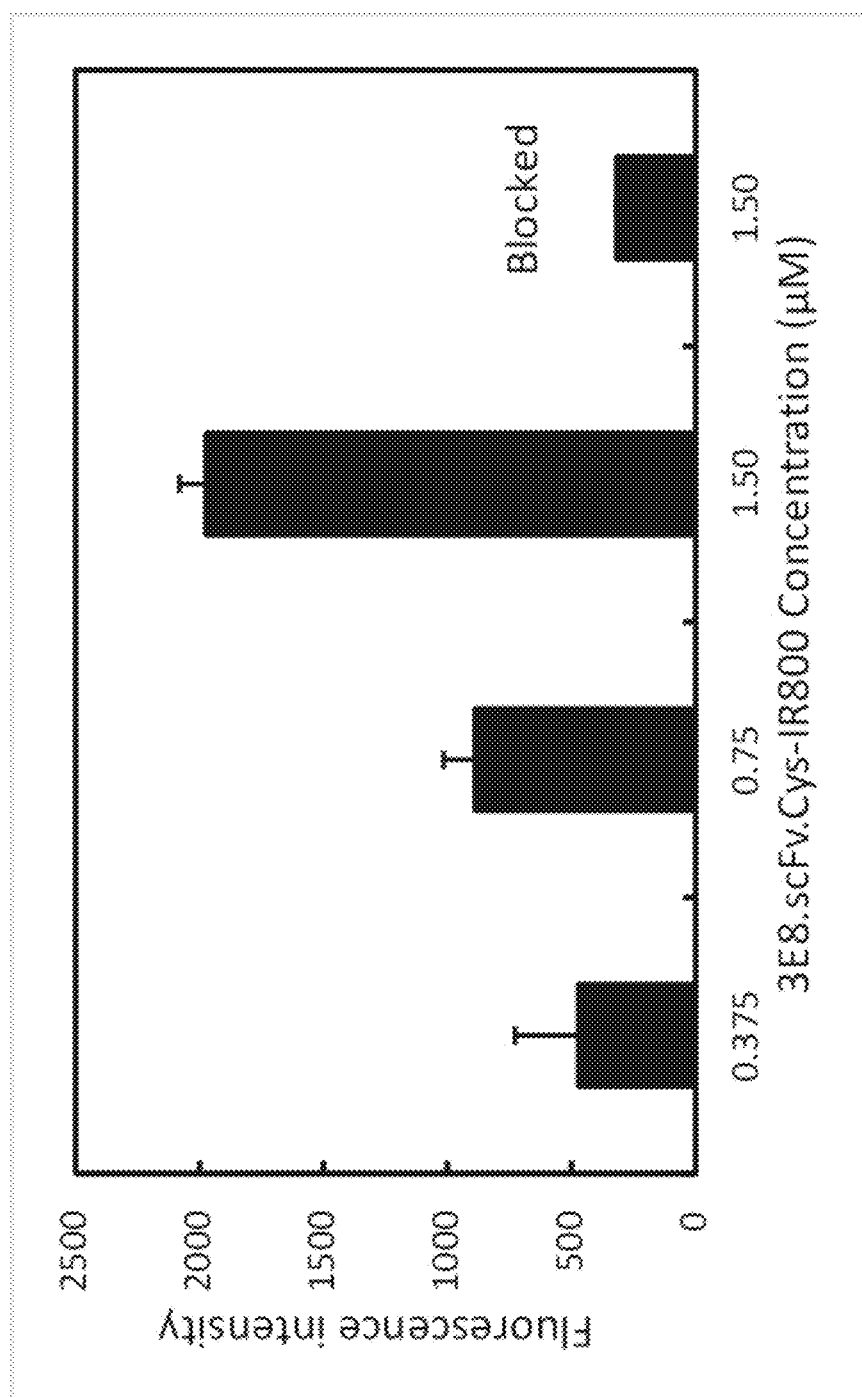

FIG. 7 shows In vitro binding of 3E8.scFv.Cys-IR800 to live LS-174 cells grown on plates. The magnitude of the bound 3E8.scFv.Cys-IR800 increased proportional to the incubation concentration. Prior incubation of cells with a fivefold excess concentration of 3E8ΔCH2 blocked 83% of the 3E8.scFv.Cys-IR800 binding.

Figure 8:
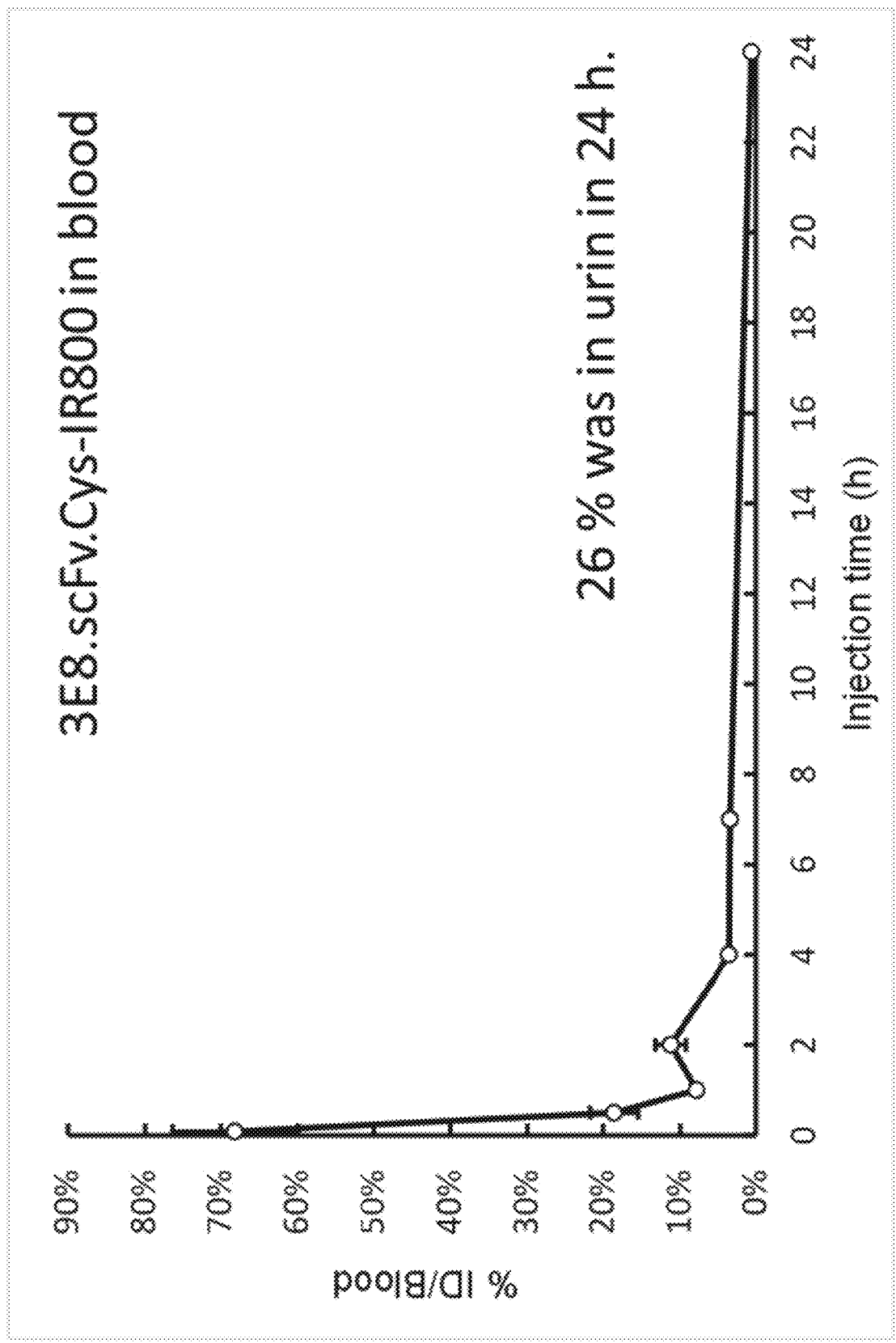

FIG. 8 shows blood clearance of 3E8.scFv.Cys-IR800 in non-tumor bearing mice showed an initial clearance half-life of ~30 min., 26% cumulative urine accumulation after 3 h, and complete clearance from blood by 24 h post i.v. administration. This shows the rapid excretion and removal from the background in the living body.

Figure 9:

FIG. 9 shows optical images detecting >800 nm emission (left) and photographs (right) of two of the mice bearing orthotopic LS-174T tumors. Mice were euthanized 24 h after i.p. administrations. The abdomen opened for imaging. Prominent tumors are indicated with arrows. The mouse labeled 3E8.scFv.Cys-IR800 was administered 1 nmol of 3E8.scFv.Cys-IR800. The Control mouse was sham injected.

Figure 10:
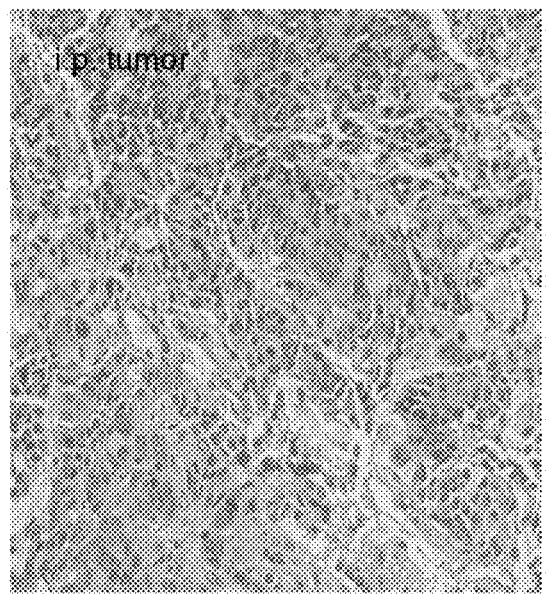

FIG. 10 shows H&E stained histology section of a visible tumor taken from mice in the experiment of FIG. 9, showing that the suspected tumors that were identified by the NIRF fluorescence from i.p injection of 3E8.scFv.Cys-IR800 are confirmed to be tumors.

Figure 11:
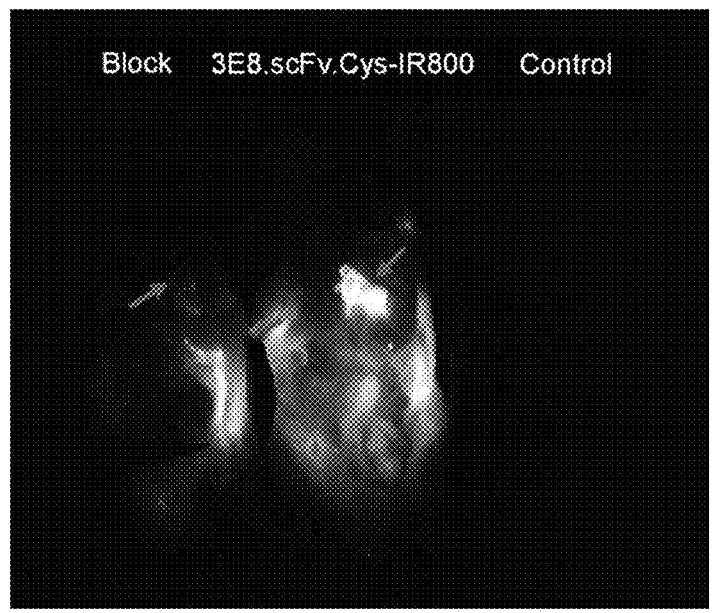

FIG. 11 shows optical images detecting >800 nm emission of three mice bearing orthotopic LS-174T tumors. Mice were euthanized 24 h after i.p. administrations and the abdomen opened for imaging. A prominent tumor is indicated with an arrow. The Control mouse was sham injected, the mouse labeled 3E8.scFv.Cys-IR800 received 1 nmol of that agent, and the mouse labeled Block received 10 nmol of 3E8ΔCH2 3 h prior to receiving 1 nmol of 3E8.scFv.Cys-IR800. This blocks the TAG-72 target with a non-fluorescent TAG-72 binding antibody fragment so that 3E8.scFv.Cys-IR800 has little TAG-72 left unoccupied by 3E8ΔCH2 and therefore cannot bind to the tumors.

Figure 12:
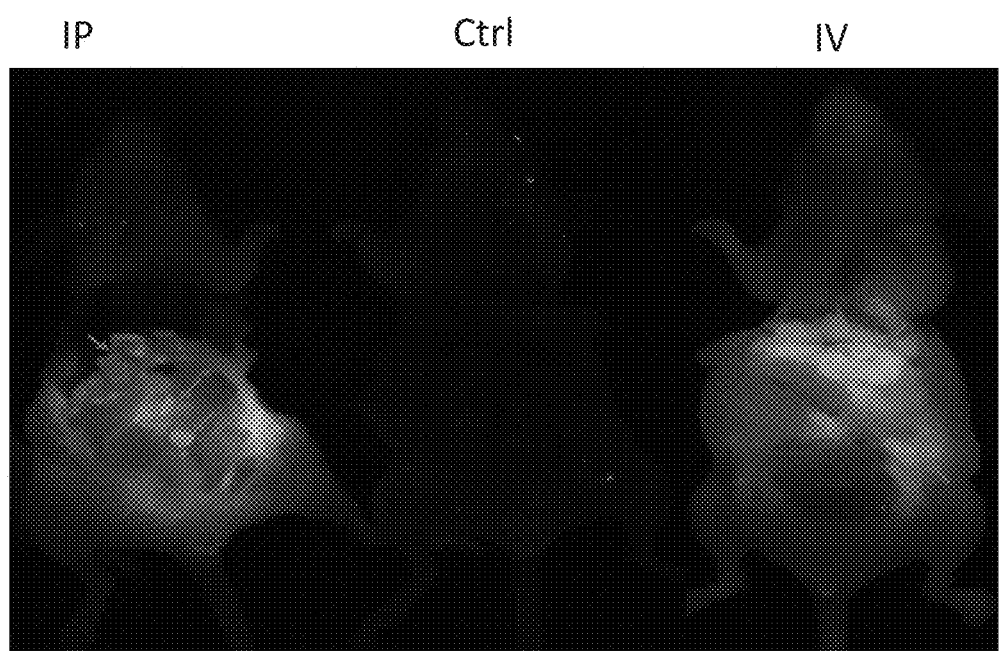

FIG. 12 shows NIRF signal comparison between i.p and i.v injection of 3E8.scFv.Cys-IR800. i.v. injection showed a predominant liver signal that can be seen in the IV mouse marked by the top arrow in the IV mouse, while the bottom arrow shows tumor with less NIRF signal than the liver. In the IP mouse the top arrow is also the liver region where only background NIRF can be detected which is lower than the signal in the tumor marked by the bottom arrow.

Figure 13:
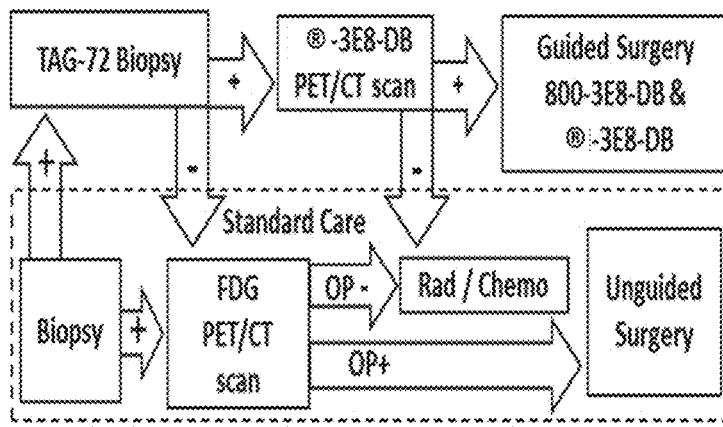

FIG. 13 shows a therapeutic process to separate and treat TAG-72 expressing colon cancer patients using 3E8 antibody fragments labeled with radionuclides and optical agents. As used in the figure "DB" refers to any antibody of fragment (such as an scFv), wherein the 3E8 antibody fragment used here is 3E8.scFv.Cys-IR800.

IV. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself.

For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. Compositions

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular anti-TAG-72 imaging agent is disclosed and discussed and a number of modifications that can be made to a number of molecules including the anti-TAG-72 imaging agent are discussed, specifically contemplated is each and every combination and permutation of anti-TAG-72 imaging agent and the modifications that are possible unless specifically indicated to the contrary. Thus, if a class of molecules A, B. and C are disclosed as well as a class of molecules D, E. and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

A breakthrough imaging approach is represented by Optical Surgical Navigation (OSN) using cancer-specific near infrared emitting imaging (NIRF) agents which report the presence of the NIRF molecules visually, in real time (<1 second), and over a wide (e.g. ~10-20 cm) field of view. In OSN with NIRF, a fluorescent molecule, usually a dicyanine NIRF dye, is conjugated to a cancer targeted molecule like an antibody directed to a cancer cell target. After systemic administration, the conjugate circulates, localizes at the cancer cells, and background washes out and is excreted leaving the targeted conjugate at the cancer cells. During surgery, a commercial NIRF optical imager uses an LED, white light or a laser light source sending incident light into the patient's tissues that includes light from 650-790 nm, preferably 75-785 nm. The NIRF dye absorbs some of that light and emits further fluorescent light at 8000-840 nm, preferably at ≥800 nm. A CCD (Charge coupled device) optical imaging camera monitors continuously for light above 800 nm and is filtered to reject all light below 800 nm, hence recording only or primarily the light emitted from the fluorescent molecule, and thus recording the position and intensity of the NIRF light in a continuous video. The video can optionally be overlaid in real time on a regular white light video of the surgical field, so that the surgeon sees on a monitor screen both the surgical field in normal colors, with the fluorescence NIRF signal overlaid in a contrasting color, showing where the cancer cells are located, and after resection, where they have been removed from. Most attempts to create OSN NIRF imaging agents targeted to colon cancer have used antibodies to promising targets: TAG-72, CEA, ILGF-1, and uPAR. These targets are all expressed on some colorectal cancers, but TAG-72 differs from other targets in being secreted from the cancer cells and pooling in the cancers extracellular spaces, hence accumulating in greater quantity and being more accessible to administered antibodies targeted to TAG-72. TAG-72 is membrane-bound glycoprotein that is expressed in 80% of colorectal cancers with relatively little expression in normal mucosa. It is expressed at high concentrations due to secretion of TAG-72 from the cancer cells and pooling in the tumor microenvironment. It also lacks a significant circulating fraction that can create background signal for an imaging agent. A radiolabeled $^{125}$I-antibody to TAG-72 was used clinically in a successful RADS study, demonstrating remarkably long adherence time (up to 1 month) at the antigen.

While all attempts to create OSN agents targeting TAG-72 reported some successful imaging of tumors in rodents, none of these attempts are useful clinically in human beings. Three reports used NIRF dyes that emit far too low in wavelength to be detected by clinical imagers, which detect only >800 nm emission. Two reports used dyes emitting in the clinically useful range, but those dyes were conjugated to the proteins by labeling methods that are not site specific, which leads to the drug product being a mixture of materials and well-known in the art problems that preclude practical usage. Site specific means that the NIRF dye binds to only one amino acid on the protein, not in general to all of one kind, like all of the lysines. Full sized antibodies additionally have very long, suboptimal circulation times in the body. Zou successfully tested a delta CH2 deleted fragment of a TAG-72-targeted CC49 antibody, which is one third smaller than a full antibody, which diminished the circulation time somewhat compared to a full antibody, but this fragment also was not site-specifically labeled and used a clinically not useful dye (emitting far below 800 nm). These larger molecular weight proteins including the delta CH2 deleted CC49 do not excrete using the renal system, and hence circulate too long and accumulate in the liver, which contains colon cancer targets bound to the NIRF dye and needing resection by the surgeon. In colon cancer liver metastases are the most common. The liver excreted antibody-NIRF dye conjugate thus creates unacceptable background NIRF signal that makes these agents not useful as NIRF targeted dyes in the field of human colon cancer NIRF imaging. The reason is that liver metastases are a primary target of colon cancer and liver excretion of optical and nuclear imaging agents creates unacceptable background signal. A new agent was created that solves all of the aforementioned deficiencies. Herein an engineered 3E8.scFv antibody fragment of 28 kDa, small enough for renal excretion, that contains a C-terminal cysteine residue (3E8.scFV.Cys described in U.S. Pat. No. 9,718,888 B2 and incorporated herein by reference in its entirety for the teachings of 3E8.scFV.Cys) was used. A NIRF dye, IRDye800-maleimide with a peak emission >800 nm that is matched to clinically used imagers was used, and a maleimide appended group that specifically reacts with the terminal cysteine on the 3E8.scFv.Cys to produce a single agent, 3E8.scFv.Cys-IR800 (FIG. 1). 3E8.scFv.Cys-IR800 is a new OSN agent targeted to TAG-72 that is the first ever discrete, 1 protein: 1 NIRF dye conjugate of 3E8.scFv.Cys. It is highly pure, labeled only at the Cys (site-specific) and maintains specific target binding to TAG-72. It was found that the product has highly specific binding to TAG-72 in plated cells and high specificity for the TAG-72 expressed in vivo in human colorectal adenoma cancer. Finally, the very surprisingly different and advantageous biodistribution of 3E8.scFv.Cys-IR800 to tumors and away from the important liver organ is demonstrated by using an intraperitoneal administration. Accordingly, in one aspect, disclosed herein are anti-TAG-72 imaging agents comprising the formula Y-R, wherein Y comprises an anti-TAG-72 binding moiety and R comprises a first detectable label; wherein the first detectable label comprises any dicyanine dye that emits fluorescent light that is detectable on a clinical optical NIRF imager at primarily above 800 nm.

C. Methods and Compositions

1. Antibodies

In one aspect, the imaging agents disclosed herein comprise anti-TAG-72 binding moieties. Such binding moieties can comprise antibodies or any fragment thereof that can bind TAG-72.
(1) Antibodies Generally
The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to interact with tumor-associated glycoprotein 72 (TAG-72). Antibodies that bind the disclosed regions of TAG-72 such as to a sialyl-Tn epitope of TAG-72 are also disclosed. The antibodies can be tested for their desired activity using the in vitro assays described herein, or by analogous methods, after which their in view therapeutic and/or prophylactic activities are tested according to known clinical testing methods. There are five major classes of human immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity.

The disclosed monoclonal antibodies can be made using any procedure which produces mono clonal antibodies. For example, disclosed monoclonal antibodies can be prepared using hybridoma methods, such as those described by Kohler and Milstein, *Nature*, 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods. DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques. e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

Native antibodies are usually heterotetrameric glycoproteins, composed of two identical light (L) chains and two identical heavy (H) chains. The disclosed TAG-72 binding molecules whether monoclonal antibodies, polyclonal antibodies, chimeric antibodies, humanized or human antibodies, as well as antibodies fragments and functional variants can comprise all or a portion of light and heavy chains. In one aspect, the disclosed anti-TAG-72 binding molecules can comprise any of the heavy and light chains disclosed herein in Table 1.

In a complete antibody, typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V(H)) followed by a number of constant (C(H)) domains. Each light chain has a variable domain at one end (V(L)) and a constant (C(L)) domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa (k) and lambda (l), based on the amino acid sequences of their constant domains. Depending on the amino acid sequence of the constant domain of their heavy chains, immunoglobulins can be assigned to different classes. There are five major classes of human immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively.

The term "variable" is used herein to describe certain domains of the heavy and light chains that differ in sequence among antibodies and are used in the binding and specificity of each particular antibody for its particular antigen. However, the variability is not usually evenly distributed through the variable domains of antibodies. The more highly conserved portions of the variable domains are called the framework (FR). The variable domains of native heavy and light chains each comprise four FR regions, largely adopting a β-sheet configuration, connected by three complementarity determining regions (CDRs), which form loops connecting, and in some cases forming part of, the β-sheet structure. The variability is typically concentrated in the CDRs or hypervariable regions both in the light chain and the heavy chain variable domains.

The CDRs in each chain are held together in close proximity by the FR regions and, with the CDRs from the other chain, contribute to the formation of the antigen binding site of antibodies (see Kabat E. A. et al., "Sequences of Proteins of Immunological Interest," National Institutes of Health, Bethesda, Md. (1987)). The term "complementary determining regions" as used herein means sequences within the variable regions of binding molecules, such as immunoglobulins, that generate the antigen binding site which is complementary in shape and charge distribution to the epitope recognized on the antigen. The CDR regions can be specific for linear epitopes, discontinuous epitopes, or conformational epitopes of proteins or protein fragments, either as present on the protein in its native conformation or, in some cases, as present on the proteins as denatured, e.g., by solubilization in SDS. Epitopes may also consist of post-translational modifications of proteins.

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415428).

As used herein, the term "antibody or fragments thereof" encompasses chimeric antibodies and hybrid antibodies, with dual or multiple antigen or epitope specificities, and fragments, such as F(ab')2, Fab', Fab, Fv, scFv, and the like, including hybrid fragments. Thus, fragments of the antibodies that retain the ability to bind their specific antigens are provided. For example, fragments of antibodies which maintain TAG-72 binding activity are included within the meaning of the term "antibody or fragment thereof." Such antibodies and fragments can be made by techniques known in the art and can be screened for specificity and activity according to the methods set forth in the Examples and in general methods for producing antibodies and screening antibodies for specificity and activity (See Harlow and Lane. *Antibodies, A Laboratory Manual*. Cold Spring Harbor Publications, New York, (1988)).

Also included within the meaning of "antibody or fragments thereof" are conjugates of antibody fragments and antigen binding proteins (single chain antibodies).

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. *Curr. Opin. Biotechnol.* 3:348-354, 1992).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

(2) Human Antibodies

The disclosed human antibodies can be prepared using any technique. The disclosed human antibodies can also be obtained from transgenic animals. For example, transgenic, mutant mice that are capable of producing a full repertoire of human antibodies, in response to immunization, have been described (see, e.g., Jakobovits et al., *Proc. Natl. Acad. Sci. USA*, 90:2551-255 (1993), Jakobovits et al., *Nature*, 362:255-258 (1993); Bruggermann et al., *Year in Immunol.*, 7:33 (1993)). Specifically, the homozygous deletion of the antibody heavy chain joining region (J(H)) gene in these chimeric and germ-line mutant mice results in complete inhibition of endogenous antibody production, and the successful transfer of the human germ-line antibody gene array into such germ-line mutant mice results in the production of human antibodies upon antigen challenge. Antibodies having the desired activity are selected using Env-CD4-co-receptor complexes as described herein.

(3) Humanized Antibodies

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an sFv, Fv, Fab, Fab', F(ab')2, or other antigen-binding portion of an antibody) which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances. Fv framework (FR) residues of the human antibody are replaced by corresponding non-human residues. Humanized antibodies may also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody (Jones et al., Nature, 321:522-525 (1986), Reichmann et al., Nature, 332:323-327 (1988), and Presta, Curr. Opin. Struct. Biol., 2:593-596 (1992)).

Methods for humanizing non-human antibodies are well known in the art. For example, humanized antibodies can be generated according to the methods of Winter and co-workers (Jones et al., Nature, 321:522-525 (1986), Riechmann et al., Nature, 332:323-327 (1988), Verhoeyen et al., Science, 239:1534-1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377 (Morgan et al.).

Therefore, in one aspect, disclosed herein are anti-TAG-72 imaging agents, wherein the anti-TAG-72 binding moiety comprises an antibody or TAG-72 binding antibody fragment (such as, for example, an scFv, F(ab')2, or Fab' that binds TAG-72). For example, the anti-TAG-72 binding moiety comprises 3E8.scFv (such as, for example, as set forth in SEQ ID NO: 1).

2. scFvs and Nucleic Acids Thereof

As noted above, in one aspect, the anti-TAG-72 imaging agents disclosed herein can comprise an anti-TAG-72 binding moiety wherein the binding moiety is a scFv. Accordingly, disclosed herein are scFvs which specifically bind tumor-associated glycoprotein 72 (TAG-72). Even more specifically, they can bind the sialyl-Tn epitope of TAG-72. These highly stable, high-affinity, bacterially-expressible scFvs are capable of specifically binding to a sialyl-Tn glycoform epitope found in TAG-72, a mucin-like glycoprotein found in human adenocarcinomas. This epitope is rarely expressed in the microenvironment of healthy tissue and thus provides a specific target for imaging and detection. Radiolabeled antibodies that specifically bind Sialyl-Tn allow one to image at the molecular level and provide the ability to improve patient care. Various molecules—B72.3, CC49, huCC49, 3E8—demonstrate the utility of anti-TAG-72 antibodies in cancer diagnosis and imaging.

3E8.scFv, a scFv that incorporates structural and binding site components from a CC49 scFv and the 3E8 antibody, as well as other sequence features for bacterial expression and purification, are described herein. Also described herein is the DNA sequence, protein sequence, and method of expression in and purification from *Escherichia coli*.

The stability of the scFv and its binding to TAG-72 in mucin is demonstrated herein. Also demonstrated is the use of biotinylated 3E8.scFv in immunohistochemistry against a human colon cancer specimen. Finally, described herein is the construction of a C-terminal Cys mutant, 3E8.scFv.Cys, and it is demonstrated that it can be specifically conjugated to a maleimide PEG. Since 3E8.scFv is derived from a humanized antibody, it is not likely to elicit a human immune response.

The scFvs disclosed herein have the following properties: tight and specific binding to the cancer epitope, sialyl-Tn (Thor 1986; Thor 1987), enhanced stability for longer shelf life, performance during application, resistance to serum proteases; improved expression and purification from bacteria; amenability to further engineering; reduced immunogenicity; and increased tissue penetrance over full-length antibodies (IgG) and fragment antigen binding (Fab) domains (Yokota 1992) Several of these properties exist in one or more sialyl-Tn binding proteins, but to date, no single molecule combines all desired features (Colcher 1999; Yoon 2006).

Specifically, the scFvs disclosed herein can have a shelf life of 1, 2, 3, 4, 5, 6, 7, 8, 9, 10, 11, or 12 weeks, or 3, 4, 5, 6, 7, 8, 9, 10, 11, or 12 months, or 1 2, 3, 4, 5, 6, 7, 8, 9, or 10 years more than a full-length antibody (IgG) or Fab domain. The scFvs disclosed herein can be 2, 3, 4, 5, 6, 7, 8, 9, or 10 times, or any amount smaller, larger or in between, more resistance to serum proteases. They can have 2, 3, 4, 5, 6, 7, 8, 9, or 10 times, or any amount smaller, larger or in between, reduced immunogenicity w % ben compared with a full length IgG or Fab domain. They can have 2, 3, 4, 5, 6, 7, 8, 9, or 10 times, or any amount smaller, larger or in between, increased tissue penetrance compared with a full length IgG or Fab domain. They can have 1, 2, or 3 or more of these characteristics.

To generate a cancer detection and imaging agent with the above features, a single chain variable fragment (scFv) has been engineered (SEQ ID NOs: 1 and 2 are examples). Full-length antibodies are large (~160 kDa) and possess innate effector functions that are not necessary, nor desirable for imaging and detection (FcRn recycling and cellular internalization, cytoxicity, etc.). Single chain variable fragments lack the constant domains responsible for effector functions, but maintain the full antigen binding domains (Bird 1988). Their small size (~25 kDa) and lack of complexity is more amenable to bacterial production, and high-throughput engineering and screening (Sandhu 1992; Pini 2000). Additionally, the compactness of scFvs and lack of cellular uptake improve tissue penetrance and provide more flexible serum half-lives. The clearance rates are faster than IgGs which is desired when using harmful radionuclides, but can be extended by PEGylation to complement a wider pairing of isotopes (Yang 2003). The 3E8-inspired scFvs disclosed herein are humanized for reduced immunogenicity, expresses well in bacteria, are 1, 2, 3, 4, 5, 6, 7, 8, 9, 10, 11, 12, 13, 14, 15, 16, 17, 18, 19, or 20° C. more stable than the clinically tested CC49.scFv, and bind the sialyl-Tn antigen with low nanomolar affinity. Accordingly, disclosed herein are anti-TAG-72 imaging agents, wherein the anti-TAG-72 binding moiety comprises an antibody or TAG-72 binding antibody fragment (such as, for example, an scFv, F(ab')2, or Fab' that binds TAG-72). For example, the anti-TAG-72 binding moiety comprises 3E8.scFv (such as, for example, as set forth in SEQ ID NO: 1).

In one aspect, the antiTAG-72 binding moiety can comprise additional residues to facilitate the addition of a detectable label. Accordingly, in one aspect disclosed herein are anti-TAG-72 imaging agents, wherein the 3E8.scFv has been modified to further comprise a terminal cysteine residue (3E8.scFv.Cys) (such as, for example, as set forth in SEQ ID NO: 2). It is understood and herein contemplated that the cysteine residue used to attach the detectable label does not have to occur at the terminal end of the scFv, but can also be inserted at the terminal end of the VH or VL prior to the linker joining the variable domains or any other site on the antibody of scFv where the label can be inserted without affecting binding to TAG-72.

It is understood and herein contemplated that the disclosed anti-TAG-72 binding moieties can comprise addition structure such as leader sequences to assist in export, linkers to join detectable labels to the binding moiety and as well as linkers to join fragments such as a VH domain and VL domain together to form a scFv. For example, the sequences of SEQ ID NOs: 1 and 2 include the pelB leader sequence for periplasmic export with the signal peptidase sequence underlined (MKYLLPTAAAGLLLLAAQPAMA (SEQ ID NO: 3)), a cleavable 6×His tag with TEV protease recognition sequence (AHHHHHHGSSGGGENLYFQ (SEQ ID NO: 4)), a short linker (GSSG (SEQ ID NO: 5)), the VL domain derived from 3E8, a linker known as 205C (LSADDAKKDAAKKDDAKKDDAKKDL (SEQ ID NO: 6)) derived from a CC49 scFv, and the VH domain derived from 3E8. As used herein, and in addition to the linkers specifically described, it is understood and herein contemplated that "linkers" can be short peptide sequences that occur between protein domains. The linkers can be flexible or rigid. Flexible linkers are often composed of flexible residues like glycine and serine so that the adjacent protein domains are free to move relative to one another. In particular, the linker can be a polyglycine (e.g. 3, 4, or 5 glycine), a polyserine (e.g. 3, 4, or 5 serine), or a combination of glycine and serine including repeating combinations. For example, the linker can be a glycine and serine linker, such as, for example, a G4S, GSG4, G2SG3SG2, G2SG, G3S linker, or any other linker known in the art where the base linker sequence can optionally be repeated 2, 3, 4, or more times. In one aspect, a linker can be used to join VH and VL segments. In another aspect, linkers can be used to link a detectable label (such as, for example a dicyanine dye) to a the anti-TAG-72 binding moiety (such as, for example, by linking to a terminal cysteine).

The scFvs disclosed herein can be made in a variety of ways, as one of skill in the art will appreciate. In its most essential form, the antibody fragment can comprise a heavy chain variable region comprising SEQ ID NO: 10, and a light chain variable region comprising SEQ ID NO: 11, or a fragment of SEQ ID NO: 10 and 11. For example, an scFv can be produced which has 60, 70, 80, 90, 91, 92, 93, 94, 95, 96, 97, 98, or 99% identity to SEQ ID NO: 10, and 60, 70, 80, 90, 91, 92, 93, 94, 95, 96, 97, 98, or 99% identity to SEQ ID NO: 11. The scFv can be functionally equivalent to those found in SEQ ID NOS 10 and 11.

The scFvs can have an antigen binding affinity for sialyl-Tn which is at least 25% that of 3E8. 3E8 has shown an anti-tumor therapeutic effect in athymic mice bearing human colon adenocarcinoma xenografts (Yoon 2006).

The presently disclosed subject matter includes functional equivalents of the antibodies of the presently disclosed subject matter. As used herein, the phrase "functional equivalent" as it refers to an antibody refers to a molecule that has binding characteristics that are comparable to those of a given antibody. In some embodiments, chimerized, humanized, and single chain antibodies, as well as fragments thereof, are considered functional equivalents of the corresponding antibodies upon which they are based.

Functional equivalents also include polypeptides with amino acid sequences substantially the same as the amino acid sequence of the variable or hypervariable regions of the antibodies of the presently disclosed subject matter. As used herein with respect to nucleic acid and/or amino acid sequences, the phrase "substantially the same" refers to a biosequence with in some embodiments at least 80%, in some embodiments at least 85%, in some embodiments at least about 90%, in some embodiments at least 91%, in some embodiments at least 92%, in some embodiments at least 93%, in some embodiments at least 94%, in some embodiments at least 95%, in some embodiments at least 96%, in some embodiments at least 97%, in some embodiments at least 98%, and in some embodiments at least about 99% sequence identity to another nucleic acid and/or amino acid sequence, as determined by the FASTA search method in accordance with Pearson & Lipman, 1988. In some embodiments, the percent identity calculation is performed over the full length of the nucleic acid and/or amino acid sequence of an antibody of the presently disclosed subject matter.

Specifically disclosed herein is an amino acid sequence comprising 90% identity to SEQ ID NO: 1. Also disclosed is an isolated amino acid sequence comprising 90% identity to SEQ ID NO: 2. Further disclosed is a nucleic acid sequence from which may be expressed an antibody fragment, such as the scFv antibodies disclosed herein. Also disclosed is nucleic acid sequence from which may be expressed the antibody fragments of the present invention. Disclosed herein is a nucleic acid sequence comprising 90% identity to SEQ ID NO: 7. Also disclosed is a nucleic acid sequence comprising 90% identity to SEQ ID NO: 8. Also disclosed is a vector comprising the nucleic acids disclosed herein. Vectors include, but are not limited to, a bare nucleic acid segment, a carrier-associated nucleic acid segment, a nucleoprotein, a plasmid, a virus, a viroid, or a transposable element. Also disclosed is a cell that produces the antibody fragment of the present invention.

Initial purification of 3E8.scFv resulted in poor yields with the majority of the antibody fragment residing in the insoluble fraction. It appeared that the amino acid sequence of SEQ ID NO: 1 was a poor substrate for signal peptidase. To improve the cleavage reaction, a second alanine codon was inserted into the DNA sequence. The resulting protein product, MKYLLPTAAAGLLLLAAQPAMAAHHHHHHGSSGGGENLYFQGSSGDIV (SEQ ID NO: 9), increases the fraction of soluble (membrane-liberated) antibody fragment.

It is understood and herein contemplated that the anti-TAG-72 imaging agents described herein can be used in methods of treating, diagnosing, prognosing, and monitoring a cancer and cancer therapies. In particular, the anti-TAG-72 imaging agents are particularly well suited to be used in optical surgical navigation (OSN) to direct treatment and monitor the efficacy of said treatment. It is further understood that the disclosed methods can be used in any cancer where TAG-72 is expressed. A representative but non-limiting list of cancers that the disclosed compositions can be used to treat is the following: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, lung cancers such as small cell lung cancer and non-small cell lung cancer, neuroblastoma/glioblastoma, ovarian cancer, skin cancer, liver cancer, melanoma, squamous cell carcinomas of the mouth, throat, larynx, and lung, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon cancer, rectal cancer, prostatic cancer, or pancreatic cancer.

3. Treatment Methods

Disclosed herein are compositions comprising an scFv and a pharmaceutically acceptable carrier. For example, disclosed are compositions useful for the treatment of cancer comprising a therapeutically effective amount of an scFv. For instance, the antibody fragment can be, directly or indirectly, associated with or linked to an effector moiety having therapeutic activity, and the composition is suitable for the treatment of cancer. The effector moiety can be a radionuclide, therapeutic enzyme, anti-cancer drug, cytokine, cytotoxin, or anti-proliferative agent.

Disclosed herein is a method for in vivo treatment of a mammal having a TAG-72-expressing cancer comprising a step of administering to the mammal a therapeutically effective amount of a composition comprising an anti-TAG-72 imaging agent. The imaging agent can be used to guide and monitor the treatment of a cancer. Thus, in one aspect, disclosed herein are methods of performing surgical removal of a tumor in a subject comprising administering to a subject the any of the anti-TAG-72 imaging agents disclosed herein (such as, for example 3E8.scFv.Cys-IR); and guiding the surgical removal of the tumor using optical surgical navigation. In some aspect, the method further comprises assaying the tumor using the anti-TAG-72 imaging agent to determine the possibility of surgical removal after administration and prior to tumor removal using optical surgical navigation. Additionally, in some aspects, disclosed herein are methods of performing surgical removal of a tumor in a subject of any preceding aspect further comprising monitoring the progress of the surgical removal. It is understood and herein contemplated that in some instances it can be advantageous to use different detectable labels to optically guide the surgical removal of a tumor and monitor the post surgical removal site for efficacy of the procedure. Accordingly, in one aspect, disclosed herein are anti-TAG-72 imaging agents, wherein the anti-TAG-72 imaging agent further comprises a second detectable label, such as, for example a radiolabel.

Additionally, disclosed herein are methods of performing optical surgical navigation comprising administering to a subject any of the anti-TAG-72 imaging agents disclosed herein, wherein the anti-TAG-72 imaging agent is used as an optical surgical navigation (OSN) agent administered intraparetoneally or intravenously.

Also disclosed is a method for suppressing tumor growth in a subject, the method comprising administering to a subject bearing a tumor an effective amount of an scFv composition, wherein the scFv is coupled to an anti-tumor composition. By "suppressing tumor growth" is meant that a tumor grows less than one which is not treated (a control). For example, suppressed tumor growth can mean that the tumor being treated grows 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, or 100% less than the measured growth of a control over the same period of time.

It is further understood that the disclosed
a) Administration

The anti-TAG-72 imaging agents of the present disclosure may be administered to a mammal in accordance with the aforementioned methods of treatment in an amount sufficient to produce such effect to a therapeutic, prophylactic, or diagnostic effect. Such antibodies of the invention can be administered to such mammal in a conventional dosage form prepared by combining the antibody of the invention with a conventional pharmaceutically acceptable carrier or vehicle, diluent, and/or excipient according to known techniques to form a suspension, injectable solution, or other formulation. It will be recognized by one of skill in the art that the form and character of the pharmaceutically acceptable carrier or diluent is dictated by the amount of active ingredient with which it is to be combined, the route of administration and other well-known variables.

Pharmaceutically acceptable formulations may include, e.g., a suitable solvent, preservatives such as benzyl alcohol if desired, and a buffer. Useful solvent may include, e.g., water, aqueous alcohols, glycols, and phosphate and carbonate esters. Such aqueous solutions contain no more than 50% by volume of organic solvent. Suspension-type formulations may include a liquid suspending medium as a carrier, e.g., aqueous polyvinylpyrrolidone, inert oils such as vegetable oils or highly refined mineral oils, or aqueous cellulose ethers such as aqueous carboxymethylcellulose. A thickener such as gelatin or an alginate may also be present, one or more natural or synthetic surfactants or antifoam agents may be used, and one or more suspending agents such as sorbitol or another sugar may be employed therein. Such formations may contain one or more adjuvants.

The route of administration of the scFv of the invention may be oral, parenteral, by inhalation or topical. The term parenteral as used herein includes intravenous, intramuscular, subcutaneous, rectal, vaginal or intraperitoneal administration. The subcutaneous, intravenous and intramuscular forms of parenteral administration are generally preferred. The daily parenteral and oral dosage regimens for employing humanized antibodies of the invention prophylactically or therapeutically will generally be in the range of about 0.005 to 100, but preferably about 0.5 to 10, milligrams per kilogram body weight per day. Accordingly, in one aspect, disclosed herein are methods of performing OSN or surgically removing a tumor from a subject comprising intravenously or intraparitoneally administering to the subject any of the anti-TAG-72 imaging agents disclosed herein (such as, for example 3E8.scFc.Cys-IR).

The scFv of the invention may also be administered by inhalation. By "inhalation" is meant intranasal and oral inhalation administration. Appropriate dosage forms for such administration, such as an aerosol formulation or a metered dose inhaler, may be prepared by conventional techniques. The preferred dosage amount of a compound of the invention to be employed is generally within the range of about 0.1 to 1000 milligrams, preferably about 10 to 100 milligrams/kilogram body weight.

The scFv of the invention may also be administered topically. By topical administration is meant non-systemic administration. This includes the administration of a humanized antibody (or humanized antibody fragment) formulation of the invention externally to the epidermis or to the buccal cavity, and instillation of such an antibody into the ear, eye, or nose, and wherever it does not significantly enter the bloodstream. By systemic administration is meant oral, intravenous, intraperitoneal, subcutaneous, and intramuscular administration. The amount of an antibody required for therapeutic, prophylactic, or diagnostic effect will, of course, vary with the antibody chosen, the nature and severity of the condition being treated and the animal undergoing treatment, and is ultimately at the discretion of the physician. A suitable topical dose of an antibody of the invention will generally be within the range of about 1 to 100 milligrams per kilogram body weight daily.

(1) Formulations

While it is possible for an antibody fragment to be administered alone, it is preferable to present it as a pharmaceutical formulation. The active ingredient may comprise, for topical administration, from 0.001% to 10% w/v, e.g., from 1% to 2% by weight of the formulation, although it may comprise as much as 10% w/w but preferably not in excess of 5% w/w and more preferably from 0.1% to 1% w/w of the formulation. The topical formulations of the present invention, comprise an active ingredient together with one or more acceptable carrier(s) therefor and optionally any other therapeutic ingredients(s). The carrier(s) must be "acceptable" in the sense of being compatible with the other ingredients of the formulation and not deleterious to the recipient thereof.

Formulations suitable for topical administration include liquid or semi-liquid preparations suitable for penetration through the skin to the site of where treatment is required, such as liniments, lotions, creams, ointments or pastes, and drops suitable for administration to the eye, ear, or nose. Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified and sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage, an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surface active such as sorbitan esters or polyoxyethylene derivatives thereof. Suspending agents such as natural gums, cellulose derivatives or inorganic materials such as silicaceous silicas, and other ingredients such as lanolin, may also be included.

Kits according to the present invention include anti-TAG-72 imaging agents as disclosed herein, and instructions for their use. Frozen or lyophilized humanized antibody fragments to be reconstituted, respectively, by thawing (optionally followed by further dilution) or by suspension in a (preferably buffered) liquid vehicle can also be used in these kits. The kits may also include buffer and/or excipient solutions (in liquid or frozen form)—or buffer and/or excipient powder preparations to be reconstituted with water—for the purpose of mixing with the humanized antibodies or humanized antibody fragments to produce a formulation suitable for administration. Thus, preferably the kits containing the humanized antibodies or humanized antibody fragments are frozen, lyophilized, pre-diluted, or pre-mixed at such a concentration that the addition of a predetermined amount of heat, of water, or of a solution provided in the kit will result in a formulation of sufficient concentration and pH as to be effective for in vivo or in vitro use in the treatment or diagnosis of cancer. Preferably, such a kit will also comprise instructions for reconstituting and using the humanized antibody or humanized antibody fragment composition to treat or detect cancer. The kit may also comprise two or more component parts for the reconstituted active composition. For example, a second component part—in addition to the humanized antibodies or humanized antibody fragments—may be bifunctional chelant, bifunctional chelate, or a therapeutic agent such as a radionuclide, which when mixed with the humanized antibodies or humanized antibody fragments forms a conjugated system therewith. The above-noted buffers, excipients, and other component parts can be sold separately or together with the kit.

It will be recognized by one of skill in the art that the optimal quantity and spacing of individual dosages of a humanized antibody or humanized antibody fragment of the invention will be determined by the nature and extent of the condition being treated, the form, route and site of administration, and the particular animal being treated, and that such optima can be determined by conventional techniques. It will also be appreciated by one of skill in the art that the optimal course of treatment, i.e., the number of doses of an antibody or fragment thereof of the invention given per day for a defined number of days, can be ascertained by those skilled in the art using conventional course of treatment determination tests.

(2) Active Agents

The compositions of the presently disclosed subject matter can comprise an active agent, wherein the active agent comprises a therapeutic moiety, a diagnostic moiety, and/or a biologically active moiety. As used herein, the phrase "active agent" thus refers to a component of the presently disclosed compositions that provides a therapeutic benefit to a subject, permits visualization of cells or tissues in which the compositions of the presently disclosed subject matter accumulate, detection of epitopes to which the presently disclosed anti-TAG-72 imaging agents bind, and/or enhances any of these activities. In some embodiments, an active agent of the presently disclosed subject matter is selected from the group consisting of a radioactive molecule (including, but not limited to radionuclides and radioisotopes), a sensitizer molecule, an imaging agent or other detectable agent, a toxin, a cytotoxin, an anti-angiogenic agent, an anti-tumor agent, a chemotherapeutic agent, an immunomodulator, a cytokine, a reporter group, and combinations thereof. It is understood that these categories are not intended to be mutually exclusive, as some radioactive molecules, for example, are also chemotherapeutic agents, some immunomodulators are cytokines, etc.

In some embodiments, an active agent comprises a chemotherapeutic. Various chemotherapeutics are known to one of ordinary skill in the art, and include, but are not limited to alkylating agents such as nitrogen mustards (e.g., Chlorambucil, Cyclophosphamide, Isofamide, Mechlorethamine, Melphalan, Uracil mustard), aziridines (e.g., Thiotepa), methanesulfonate esters (e.g., Busulfan), nitroso ureas (e.g., Carmustine, Lomustine, Streptozocin), platinum complexes (e.g., Cisplatin, Carboplatin), and bioreductive alkylators (e.g., Mitomycin C, Procarbazine); DNA strand breaking agents (e.g., Bleomycin); DNA topoisomerase 1 inhibitors (e.g., camptothecin and derivatives thereof including, but not limited to 10-hydroxycamptothecin), DNA topoisomerase II inhibitors (e.g., Amsacrine, Dactinomycin, Daunorubicin, Doxorubicin, Idarubicin, Mitoxantrone, Etoposide, Teniposide, Podophyllotoxin); DNA minor groove binders (e.g., Plicamycin); anti-metabolites such as folate antagonists (e.g., Methotrexate and trimetrexate), pyrimidine antagonists (e.g., Fluorouracil, Fluorodeoxyuridine, CB3717, Azacytidine, Cytarabine, Floxuridine), purine antagonists (e.g., Mercaptopurine, 6-Thioguanine, Fludarabine, Pentostatin), sugar modified analogs (e.g., Cyctrabine, Fludarabine), and ribonucleotide reductase inhibitors (e.g., Hydroxyurea); tubulin interactive agents (e.g., Vincristine, Vinblastine, Paclitaxel); adrenal corticosteroids (e.g., Prednisone, Dexamethasone, Methylprednisolone, Prednisolone); hormonal blocking agents such as estrogens and related compounds (e.g., Ethinyl Estradiol, Diethylstilbesterol, Chlorotrianisene, Idenestrol), progestins (e.g., Hydroxyprogesterone caproate, Medroxyprogesterone, Megestrol), androgens (e.g., Testosterone, Testosterone propionate; Fluoxymesterone, Methyltestosterone), leutinizing hormone releasing hormone agents and/or gonadotropin-releasing hormone antagonists (e.g., Leuprolide acetate; Goserelin acetate), anti-estrogenic agents (e.g., Tamoxifen), anti-androgen agents (e.g., Flutamide), and anti-adrenal agents (e.g., Mitotane, Aminoglutethimide). Other chemotherapeutics include, but are not limited to Taxol, retinoic acid and derivatives thereof (e.g., 13-cis-retinoic acid, all-trans-retinoic acid, and 9-cis-retinoic acid), sulfathiazole, mitomycin C, mycophenolic acid, sulfadiethoxane, and gemcitabine (4-amino-1-(2-deoxy-2,2-difluoro-D-eryi/7ro-pentofuranosyl)pyhmidin-2(1H)-on-2',2'-difluoro-2'-deoxycytidine).

The subject anti-TAG-72 imaging agents may also be administered in combination with other anti-cancer agents, e.g., other antibodies or drugs. Also, the subject humanized anti-TAG-72 binding moieties of the disclosed anti-TAG-72 imaging agents may be directly or indirectly attached to effector having therapeutic activity. Suitable effector moieties include by way of example cytokines (IL-2. TNF, interferons, colony stimulating factors. IL-1, etc.), cytotoxins (*Pseudomonas* exotoxin, ricin, abrin, etc.), radionuclides, such as $^{90}Y$, $^{131}I$, $^{99m}Tc$, $^{111}In$, $^{125}I$, among others, drugs (methotrexate, daunorubicin, doxorubicin, etc.), immunomodulators, therapeutic enzymes (e.g., beta-galactosidase), anti-proliferative agents, etc.), The attachment of antibodies to desired effectors is well known. See. e.g., U.S. Pat. No. 5,435,990 to Cheng et al. Moreover, bifunctional linkers for facilitating such attachment are well known and widely available. Also, chelators (chelants and chelates) providing for attachment of radionuclides are well known and available.

The compositions of the presently disclosed subject matter can further comprise a drug carrier to facilitate drug preparation and administration. Any suitable drug delivery vehicle or carrier can be used, including but not limited to a gene therapy vector (e.g., a viral vector or a plasmid), a microcapsule, for example a microsphere or a nanosphere (Manome et al., 1994; Hallahan et al., 2001 b; Saltzman & Fung, 1997), a peptide (U.S. Pat. Nos. 6,127,339 and 5,574,172), a glycosaminoglycan (U.S. Pat. No. 6,106,866), a fatty acid (U.S. Pat. No. 5,994,392), a fatty emulsion (U.S. Pat. No. 5,651,991), a lipid or lipid derivative (U.S. Pat. No. 5,786,387), collagen (U.S. Pat. No. 5,922,356), a polysaccharide or derivative thereof (U.S. Pat. No. 5,688,931), a nanosuspension (U.S. Pat. No. 5,858,410), a polymeric micelle or conjugate (Goldman et al., 1997; U.S. Pat. Nos. 4,551,482; 5,714,166; 5,510,103; 5,490,840; and 5,855,900), and a polysome (U.S. Pat. No. 5,922,545).

The disclosed anti-TAG-72 imaging agents can also be coupled to drugs or drug carriers using methods known in the art, including but not limited to carbodiimide conjugation, esterification, sodium periodate oxidation followed by reductive alkylation, and glutaraldehyde crosslinking (see e.g., U.S. Pat. No. 6,071,890; and European Patent No. 0 439 095).

4. Detection Methods

Disclosed are compositions suitable for the in vivo or in vitro detection of cancer comprising a diagnostically effective amount of an scFv disclosed herein. The scFv can be, directly or indirectly, associated with or linked to a detectable label, and the composition can be suitable for detection of cancer. Also disclosed is a method for in vitro immunodetection of TAG-72-expressing cancer cells comprising a step of contacting the cancer cells with a composition comprising an scFv of the present invention. The scFv can be bound to a solid support, for example.

Also disclosed is a method of in vivo immunodetection of TAG-72-expressing cancer cells in a mammal comprising a step of administering to the mammal a diagnostically effective amount of a composition comprising the scFv of the present invention.

For diagnostic applications, a detectable amount of a composition of the presently disclosed subject matter is administered to a subject. A "detectable amount", as used herein to refer to a composition, refers to a dose of such a composition that the presence of the composition can be determined in vivo or in vitro. A detectable amount will vary according to a variety of factors, including but not limited to chemical features of the composition being labeled, the detectable label, the labeling methods, the method of imaging and parameters related thereto, metabolism of the labeled drug in the subject, the stability of the label (including, but not limited to the half-life of a radionuclide label), the time elapsed following administration of the composition prior to imaging, the route of administration, the physical condition and prior medical history of the subject, and the size and longevity of the tumor or suspected tumor. Thus, a detectable amount can vary and can be tailored to a particular application. After study of the present disclosure, it is within the skill of one in the art to determine such a detectable amount.

As used herein, the terms "detectable moiety", "detectable label", and "detectable agent" refer to any molecule that can be detected by any moiety that can be added to an antibody fragment that allows for the detection of the antibody fragment in vitro and/or in vivo. Representative detectable moieties include, but are not limited to, chromophores, fluorescent moieties, enzymes, antigens, groups with specific reactivity, chemiluminescent moieties, and electrochemically detectable moieties, etc. In some embodiments, the antibodies are biotinylated.

Detection and imaging of the antibody fragment is tunable, such that imaging can be performed in under 1, 2, 4, 6, 12, or 18, 24, 36, or 48 hours, or any amount below, above, or between this amount. It has been demonstrated that PEGs/larger fragments increase serum half-life by 2, 3, 4, 5, 6, 7, 8, 9, 10, 15, 20, 25, 30, 35, 40, 45, 50, 55, 60, 65, 70, 75, 80, 85, 90, 95, or 100%, or 2, 3, 4, 5, 6, 7, 8, 9, or 10 or more times compared to a smaller fragment. This allows for imaging at different time points. For therapeutic purposes, it allows for an increase in the therapeutic window.

In one aspect, disclosed herein are methods of performing optical surgical navigation comprising administering to a subject the anti-TAG-72 imaging agent of any preceding aspect, wherein the anti-TAG-72 imaging agent is used as an optical surgical navigation (OSN) agent administered intraparetoneally or intravenously.

a) Detectable Labels

In some embodiments, a detectable label (also referred to as a detectable moiety) comprises a fluorophore. As used herein, a label can include a fluorescent dye, a member of a binding pair, such as biotin/streptavidin, a metal (e.g., gold), or an epitope tag that can specifically interact with a molecule that can be detected either in vivo (e.g., after administration to a subject) and/or in vitro, such as by producing a colored substrate or fluorescence and further does not negatively impact the ability of the antibody fragment to bind to its epitope. Substances suitable for detectably labeling proteins include fluorescent dyes (also known herein as fluorochromes and fluorophores) and enzymes that react with colorometric substrates (e.g., horseradish peroxidase). The use of fluorescent dyes is generally preferred in the practice of the invention as they can be detected at very low amounts. Furthermore, in the case where multiple antigens are reacted with a single array, each antigen can be labeled with a distinct fluorescent compound for simultaneous detection. Labeled spots on the array are detected using a fluorimeter, the presence of a signal indicating an antigen bound to a specific antibody.

Fluorophores are compounds or molecules that luminesce. Typically fluorophores absorb electromagnetic energy at one wavelength and emit electromagnetic energy at a second wavelength. Representative fluorophores include, but are not limited to, 1,5 IAEDANS; 1,8-ANS; 4-Methylumbelliferone; 5-carboxy-2,7-dichlorofluorescein; 7-dimethylaminocoumarin-3-carboxylic acid; 5-Carboxyfluorescein (5-FAM); 5-Carboxynapthofluorescein; 5-Carboxytetramethylrhodamine (5-TAMRA); 5-Hydroxy Tryptamine (5-HAT); 5-carboxy-X-rhodamine (5-ROX); 6-carboxy-X-rhodamine (6-ROX); 6-Carboxyrhodamine 6G; 6-CR 6G; 6-JOE; 7-Amino-4-methylcoumarn; 7-Aminoactinomycin D (7-AAD); 7-Hydroxy-4-I methylcoumarin; 9-Amino-6-chloro-2-methoxyacridine (ACMA); ABQ; Acid Fuchsin; Acridine Orange; Acridine Red; Acridine Yellow; Acriflavin; Acriflavin Feulgen SITSA; Aequorin (Photoprotein); AFPs—AutoFluorescent Protein—(Quantum Biotechnologies) see sgGFP, sgBFP; Alexa Fluor 350™; Alexa Fluor 405™; Alexa Fluor 430™; Alexa Fluor 488™; Alexa Fluor 500™; Alexa Fluor 514™; Alexa Fluor 532™; Alexa Fluor 546™; Alexa Fluor 555™; Alexa Fluor 568™; Alexa Fluor 594™; Alexa Fluor 610™; Alexa Fluor 633™; Alexa Fluor 647™; Alexa Fluor 660™; Alexa Fluor 680™; Alexa Fluor 700™; Alexa Fluor 750™; Alexa Fluor 790™; Alizarin Complexon; Alizarin Red; Allophycocyanin (APC); AMC, AMCA-S; Aminomethylcoumarin (AMCA); AMCA-X; Aminoactinomycin D; Aminocoumarin; Anilin Blue; Anthrocyl stearate, APC-Cy7; APTRA-BTC; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H); Blue Fluorescent Protein; BFP/GFP FRET; Bimane; Bisbenzemide; Bisbenzimide (Hoechst); bis-BTC; Blancophor FFG; Blancophor SV; BOBO™-1; BOBO™-3; Bodipy492/515; Bodipy493/503; Bodipy500/510; Bodipy; 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-L; BO-PRO™-3; Brilliant Sulphoflavin FF; BTC; BTC-5N; Calcein; Calcein Blue; Calcium Crimson –; Calcium Green; Calcium Green-1 $Ca^{2+}$ Dye; Calcium Green-2 $Ca^{2+}$; Calcium Green-5N $Ca^{2+}$; Calcium Green-C18 $Ca^{2+}$; Calcium Orange; Calcofluor White; Cascade Blue™; Cascade Yellow; Catecholamine; CCF2 (GeneBlazer); CFDA; CFP (Cyan Fluorescent Protein); CFP/YFP FRET; Chlorophyll; Chromomycin A; Chromomycin A; cinnamic acid; CL-NERF; CMFDA; Coelenterazine; Coelenterazine cp; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM I Methylcoumarin; CTC; CTC Formazan; Cy2™; Cy3.1 8; Cy3.5™; Cy3™; Cy5.1 8; Cy5.5™; Cy5™; Cy7™; Cyan GFP; red cyanine dyes, Cy5/Alexa 647, cyclic AMP Fluorosensor (FiCRhR); Dabcyl; Dabsyl chloride; Dansyl; Dansyl Amine; Dansyl Cadaverine; Dansyl Chloride; Dansyl DHPE; Dansyl fluoride; 4',6-diamidino-2-phenylindole (DAPI); Dapoxyl; Dapoxyl 2; Dapoxyl 3'DCFDA; DCFH (Dichlorodihydrofluorescein Diacetate); DDAO; DHR (Dihydorhodamine 123), Di-4-ANEPPS; Di-8-ANEPPS (non-ratio); DiA (4-Di 16-ASP); Dichlorodihydrofluorescein Diacetate (DCFH); DiD-Lipophilic Tracer; DiD (DilC18(5)); DIDS; Dihydorhodamine 123 (DHR); Dil (DilC18(3)); I Dinitrophenol; DiO (DiOC18(3)); DiR; DiR (DilC18(7)); DM-NERF (high pH); DNP; Dopamine; Dronpa; bsDronpa; DsRed; DTAF; DY-630-NHS; DY-635-NHS; EBFP; ECFP; EGFP; ELF 97; EOS, Eosin; Erythrosin; Erythrosin ITC; Ethidium Bromide; Ethidium homodimer-1 (EthD-1); Euchrysin; EukoLight; Europium (111) chloride; enhanced yellow fluorescent protein (EYFP); Fast Blue; FDA; Feulgen (Pararosaniline); FIF (Formaldehyde Induced Fluorescence); FITC; Flazo Orange; Fluo-3; Fluo-4; Fluorescein (FITC); Fluorescein Diacetate; fluorescein carboxylic acid; Fluoro-Emerald; Fluoro-Gold (Hydroxystilbamidine); Fluor-Ruby; FluorX; FM 1-43™; FM 4-46; Fura Red™ (high pH); Fura Red™/Fluo-3; Fura-2;

Fura-2/BCECF; Genacryl Brilliant Red B; Genacryl Brilliant Yellow 10GF; Genacryl Pink 3G; Genacryl Yellow 5GF; GeneBlazer; (CCF2); GFP (S65T); GFP red shifted (rsGFP); GFP wild type' non-UV excitation (wtGFP); GFP wild type, UV excitation (wtGFP); GFPuv; Gloxalic Acid; Granular blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1 low calcium; Indocyanine Green, Indodicarbocyanine (DiD); Indotricarbocyanine (DiR); Intrawhite Cf; Li-COr dyes; IR-800 CW; IR-800 Mal; IRdye800JC-1; JO JO-1; JO-PRO-1; SO456; ZW800 and its zwitterionic derivatives; LaserPro; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1, LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-lndo-1; Magnesium Green; Magnesium Orange; Malachite Green; Marina Blue; I Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); nitrobenzodiazolamine (NBD); NBD Amine; Nile Blue; Nile Red; NIR641, NIR664, NIT7000, and NIR782Nitrobenzoxedidole; Noradrenaline; Nuclear Fast Red; i Nuclear Yellow; Nylosan Brilliant lavin E8G; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed (Red 613); Phloxin B (Magdala Red); Phonvite AR; Phonvite BKL; Phorwite Rev; Phorwite RPA; Phosphine 3R; PhotoResist; Phycoerythrin B [PE]; Phycoerythrin R [PE]; PKH26 (Sigma); PKH67; PMIA; Pontochrome Blue Black; POPO-1; POPO-3; PO-PRO-1; PO-I PRO-3; Primuline; Procion Yellow; Propidium Iodid (Pl); PyMPO; Pyrene; Pyronine; Pyronine B; Pyrozal Brilliant Flavin 7GF; QSY 7; Quinacrine Mustard; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine; Phalloidine; Rhodamine Red; Rhodamine WT; Rose Bengal; R-phycocyanine; R-phycoerythrin (PE); rsGFP; S65A; S65C; S65L; S65T; Sapphire GFP; SBFI; Serotonin; Sevron Brilliant Red 2B; Sevron Brilliant Red 4G; Sevron I Brilliant Red B; Sevron Orange; Sevron Yellow L; sgBFP™ (super glow BFP); sgGFP™ (super glow GFP); SITS (Primuline; Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red, SPQ (6-methoxy-N-(3 sulfopropyl) quinolinium); Stilbene; Sulphorhodamine B and C; Sulphorhodamine Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylcarboxyrhodamine; Tetraethylsulfohodamine; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TON; Thiolyte; Thiozole Orange; Tinopol CBS (Calcofluor White); TIER; TO-PRO-1; TO-PRO-3; TO-PRO-5; TOTO-1; TOTO-3; TriColor (PE-Cy5); TRITC TetramethylRodaminelsoThioCyanate; True Blue; Tru Red; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO 3; YOYO-1; YOYO-3; ZW-800; Sybr Green; Thiazole orange (interchelating dyes); semiconductor nanoparticles such as quantum dots; or caged fluorophore (which can be activated with light or other electromagnetic energy source), or a combination thereof.

Fluorophores emit energy throughout the visible spectrum; however, the best spectrum for in vivo imaging is in the near-infrared (NIR) region (650 nm-900 nm). Unlike the visible light spectrum (400-650 nm), in the NIR region, light scattering decreases and photo absorption by hemoglobin and water diminishes, leading to deeper tissue penetration of light. Furthermore, tissue auto-fluorescence is low in the NIR spectra, which allows for a high signal to noise ratio. There is a range of small molecule organic fluorophores with excitation and emission spectra in the NIR region. Some, such as indocyanine green (ICG) and cyanine derivatives Cy5.5 and Cy7, have been used in imaging for a relatively long time. Modern fluorophores are developed by various biotechnology companies and include: Li-COr dyes; IR-800 CW; IR-800 Mal; Alexa dyes; IRDye dyes; VivoTag dyes and HylitePlus dyes. For use in optical surgical navigation, it is not sufficient that the dye used emits in the near infra-red spectrum, but needs to emit above 780 nm and can extend into the near infrared II (NIR-II) spectrum from 1000 nm to 1700 nm. Preferably, the dye emits fluorescent light from about 800 nm to about 1700 nm. An example of a detectable labels that emits between 780 nm and 1700 nm include dicyanine dye. Dicyanine dyes that are useful in this invention include IRdye800, AlexaFluor 790, ZW-800 (Frangioni et al), Indocyanine Green, 50456, and the like, provided their emission peak is at least 79% nm and preferably greater than 790 nm, most preferably separated from the absorption peak by more than 15 nm, most preferably 19-35 nm, and that primarily the emitted fluorescent light is above 800 nm.

For diagnostic applications (including but not limited to detection applications and imaging applications), the antibodies of the presently disclosed subject matter can be labeled with a detectable moiety. The detectable moiety can be any one that is capable of producing, either directly or indirectly, a detectable signal. For example, a detectable moiety can be a radioisotope, such as but not limited to $^{3}$H, $^{99m}$Tc, $^{67}$Ga, $^{68}$Ga, $^{66}$Ga, $^{47}$Sc, $^{51}$Cr, $^{141}$Ce, $^{111}$In, $^{18}$F, $^{11}$C, $^{14}$C, $^{13}$N, $^{15}$N, $^{17}$O, $^{32}$P, $^{35}$S, $^{168}$Yb, $^{175}$Yb, $^{140}$La, $^{90}$Y, $^{88}$Y, $^{86}$Y, $^{153}$Sm, $^{166}$Ho, $^{165}$Dy, $^{166}$Dy, $^{62}$Cu, $^{64}$Cu, $^{65}$Cu, $^{67}$Cu, $^{77}$Br, $^{80m}$Br, $^{95}$Ru, $^{97}$Ru, $^{103}$Ru, $^{105}$Ru, $^{107}$Hg, $^{99m}$Re, $^{105}$Re, $^{101}$Re, $^{186}$Re, $^{188}$Re, $^{123}$I, $^{124}$I, $^{125}$I, $^{131}$I, $^{133}$I, $^{111}$In, $^{113m}$In, $^{121m}$Te, $^{122m}$Te, $^{125m}$Te, $^{165}$Tm, $^{168}$Tm, $^{167}$Tm, $^{203}$Hg, $^{203}$Pb, $^{211}$Bi, $^{212}$Bi, $^{213}$Bi, $^{214}$Bi, $^{225}$Ac, $^{210}$At, $^{210}$At, $^{211}$At, $^{105}$Rh, $^{109}$Pd, $^{117m}$Sn, $^{149}$Pm, $^{153}$Sm, $^{161}$Tb, $^{177}$Lu, $^{198}$Au, $^{199}$Au, $^{89}$Zr; a fluorescent or chemiluminescent compound such as but not limited to fluorescein isothiocyanate, rhodamine, or luciferin; or an enzyme, such as but not limited to alkaline phosphatase, β-galactosidase, or horseradish peroxidase.

The presently disclosed subject matter further provides methods for diagnosing a tumor, wherein a tumor sample or biopsy is evaluated in vitro. In some embodiments, a targeting ligand of the presently disclosed subject matter comprises a detectable label such as a fluorescent label, an epitope tag, or a radioactive label, each described briefly herein below.

b) Detection of an Epitope Tag

If an epitope label has been used, a protein or compound that binds the epitope can be used to detect the epitope. A representative epitope label is biotin, which can be detected by binding of an avidin-conjugated fluorophore, for example avidin-FITC. Alternatively, the label can be detected by binding of an avidin-horseradish peroxidase (HRP) streptavidin conjugate, followed by colorimetric detection of an HRP enzymatic product. The production of a colorimetric or luminescent product/conjugate is measurable using a spectrophotometer or luminometer, respectively.

c) Autoradiographic Detection

It is understood and herein contemplated that the disclosed anti-TAG-72 imaging agents can further comprises a second detectable label, such as, for example a radiolabel. In the case of a radioactive label (e.g., $^{131}$I or $^{99m}$Tc) detection can be accomplished by conventional autoradiography or by using a phosphorimager as is known to one of skill in the art. For radioactive labels, a modifier unit such as a radionuclide can be incorporated into or attached directly to any of the compounds described herein by halogenation. Examples of radionuclides useful in this embodiment include, but are not limited to tritium, $^{99m}$Tc, $^{67}$Ga, $^{68}$Ga, $^{66}$Ga, $^{47}$Sc, $^{51}$Cr, $^{141}$Ce, $^{111}$In, $^{18}$F, $^{11}$C, $^{14}$C, $^{13}$N, $^{15}$N, $^{17}$O, $^{32}$P, $^{35}$S, $^{168}$Yb, $^{175}$Yb, $^{140}$La, $^{90}$Y, $^{88}$Y, $^{86}$Y, $^{153}$Sm, $^{166}$Ho, $^{165}$Dy, $^{166}$Dy, $^{62}$Cu, $^{64}$Cu, $^{65}$Cu, $^{67}$Cu, $^{77}$Br, $^{80m}$Br, $^{95}$Ru, $^{97}$Ru, $^{103}$Ru, $^{105}$Ru, $^{107}$Hg, $^{99m}$Re, $^{105}$Re, $^{101}$Re, $^{186}$Re, $^{188}$Re, $^{123}$I, $^{124}$I, $^{125}$I, $^{131}$I, $^{133}$I, $^{111}$In, $^{113m}$In, $^{121m}$Te, $^{122m}$Te, $^{125m}$Te, $^{165}$Tm, $^{168}$Tm, $^{167}$Tm, $^{203}$Hg, $^{203}$Pb, $^{2111}$Bi, $^{212}$Bi, $^{213}$Bi, $^{214}$Bi, $^{225}$Ac, $^{210}$At, $^{210}$At, $^{211}$At, $^{105}$Rh, $^{109}$Pd, $^{117m}$Sn, $^{149}$Pm, $^{153}$Sm $^{161}$Tb, $^{177}$Lu, $^{198}$Au, $^{199}$Au, $^{89}$Zr. In another aspect, the radionuclide can be attached to a linking group or bound by a chelating group, which is then attached to the compound directly or by means of a linker. Examples of radionuclides useful in the apset include, but are not limited to tritium. $^{99m}$Tc, $^{67}$Ga, $^{68}$Ga, $^{66}$Ga, $^{47}$Sc, $^{51}$Cr, $^{141}$Ce, $^{111}$In, $^{18}$F, $^{11}$C, $^{14}$C, $^{13}$N, $^{15}$N, $^{17}$O, $^{32}$P, $^{35}$S, $^{168}$Yb, $^{175}$Yb, $^{140}$La, $^{90}$Y, $^{88}$Y, $^{86}$Y, $^{153}$Sm, $^{166}$Ho, $^{165}$Dy, $^{166}$Dy, $^{62}$Cu, $^{64}$Cu, $^{65}$Cu, $^{67}$Cu, $^{77}$Br, $^{80m}$Br, $^{95}$Ru, $^{97}$Ru, $^{103}$Ru, $^{105}$Ru, $^{107}$Hg, $^{99m}$Re, $^{105}$Re, $^{101}$Re, $^{186}$Re, $^{188}$Re, $^{123}$I, $^{124}$I, $^{125}$I, $^{131}$I, $^{133}$I, $^{111}$In, $^{113m}$In, $^{121m}$Te, $^{122m}$Te, $^{125m}$Te, $^{165}$Tm, $^{168}$Tm, $^{167}$Tm, $^{203}$Hg, $^{203}$Pb, $^{211}$Bi, $^{212}$Bi, $^{213}$Bi, $^{214}$Bi, $^{225}$Ac, $^{210}$At, $^{210}$At, $^{211}$At, $^{105}$Rh, $^{109}$Pd, $^{117m}$Sn, $^{149}$Pm, $^{153}$Sm $^{161}$Tb, $^{177}$Lu, $^{198}$Au, $^{199}$Au, and/or $^{89}$Zr. Radiolabeling techniques such as these are routinely used in the radiopharmaceutical industry. The choice of isotope will be determined based on the desired therapeutic or diagnostic application. For example, for diagnostic purposes (e.g., to diagnose and monitor therapeutic progress in primary tumors and metastases), suitable radionuclides include $^{64}$Cu, $^{67}$Ga, $^{68}$Ga, $^{66}$Ga, $^{99m}$Tc, and $^{111}$In, $^{18}$F, $^{89}$Zr, $^{123}$I, $^{131}$I, $^{124}$I, $^{177}$Lu, $^{15}$N, $^{17}$O. For therapeutic purposes (e.g., to provide radiotherapy for primary tumors and metastasis related to cancers of the prostate, breast, lung, etc.), suitable radionuclides include $^{64}$Cu, $^{90}$Y, $^{105}$Rh, $^{111}$In, $^{117m}$Sn, $^{149}$Pm, $^{153}$Sm, $^{161}$Tb, $^{166}$Dy, $^{166}$Ho, $^{75}$Yb, $^{177}$Lu, $^{186/188}$Re, $^{199}$Au, $^{131}$I, and $^{125}$I, $^{212}$Bi, and $^{211}$At.

The radiolabeled compounds are useful as imaging agents to diagnose neurological disease (e.g., a neurodegenerative disease) or a mental condition or to follow the progression or treatment of such a disease or condition in a mammal (e.g., a human). The radiolabeled compounds described herein can be conveniently used in conjunction with imaging techniques such as positron emission tomography (PET) or single photon emission computerized tomography (SPECT).

A preferred autoradiographic method employs photostimulable luminescence imaging plates (Fuji Medical Systems of Stamford, Connecticut. United States of America). Briefly, photostimulable luminescence is the quantity of light emitted from irradiated phosphorous plates following stimulation with a laser during scanning. The luminescent response of the plates is linearly proportional to the activity.

Any method known in the art for conjugating an antibody to a detectable moiety can be employed.

In some instances, the use of a dual labeled imaging agent or two separate labeled entities is beneficial to the practicing physician allowing for different labels to be used for the targeting of treatment and monitoring of said treatment. For example, the imaging agent can be administered for surgical removal using optical surgical navigation (OSN) where the same anti-TAG-72 antibody (or fragment thereof such as the 3E8.scFv.Cys-IR800 imaging agent disclosed herein) can be used to determine if surgical removal is a viable option, guide surgical removal of the tumor and then monitor and assess the efficacy of the removal procedure. In one aspect, the second label can be a radiolabel such as a radioactive iodine. Thus, in one aspect, disclosed herein are methods of performing optical surgical navigation using any of the anti-TAG-72 imaging agents disclosed herein.

Methods for iodinating any of the anti-TAG-72 imaging agents disclosed herein can comprise providing an anti-TAG-72 imaging agents comprising a tyrosine residue; and reacting the anti-TAG-72 imaging agents with a chloramine and an iodine source under conditions effective to form an iodinated anti-TAG-72 imaging agent. The resulting iodinated anti-TAG-72 imaging agent can comprise an iodinated tyrosine residue.

The chloramine can be any suitable chloramine that is compatible with the methods described herein. In some embodiments, the chloramine can comprise an organic chloramine. In some of these cases, the organic chloramine can be a non-aromatic chloramine (i.e., the chloramine does not include an aromatic moiety, such as a phenyl group). For example, the organic chloramine can comprise an alkylchloramine, such as methylchloramine, dimethylchloramine, ethylchloramine, diethylchloramine, or a combination thereof. In other embodiments, the organic chloramine can comprise an N-chloro amino acid. The N-chloro amino acid can comprise an N-monochloro amino acid or an N-dichloro amino acid, such as glycine, lysine, alanine, leucine, isoleucine, serine, glutamine, etc. In other embodiments, the organic chloramine can comprise an N-chloro peptide, such as an N-monochloro or an N-dichloro derivative of an oligopeptide such diglycine, alanylalanine, or glycylalanaine. In other embodiments, the chloramine can comprise an inorganic chloramine, such as monochloramine, dichloramine, trichloramine, or a combination thereof.

In some embodiments, the chloramine can have a molar mass of less than 250 g/mol (e.g., less than 200 g/mol, less than 150 g/mol, or less than 100 g/mol). In certain embodiments, the chloramine can have a molar mass of from 50 g/mol to 250 g/mol (e.g., from 50 g/mol to 200 g/mol, from 50 g/mol to 150 g/mol, or from 50 g/mol to 100 g/mol). In certain embodiments, the chloramine can comprise monochloramine.

The iodine source can comprise any suitable iodine source. Appropriate iodine sources can be selected in view of a number of factors, including the desired isotope of iodine to be incorporated into the iodinated anti-TAG-72 imaging agent. In some cases, the iodine source can include isotope that undergoes beta decay (e.g., beta minus decay or beta plus decay). In some cases, the iodine source can include isotope that undergoes gamma decay. For example, in some embodiments, the iodine source can include $^{123}$I, $^{124}$I, $^{125}$I, or $^{131}$I. In certain embodiments, the iodine source can comprise an iodide salt (e.g., an alkali metal salt), such as sodium iodide or potassium iodide. For example, the iodide salt can comprise [$^{123}$I] NaI, [$^{124}$I] NaI, [$^{125}$I] NaI, [$^{131}$I] NaI, [$^{123}$I] KI, [$^{124}$I] KI, [$^{125}$I] KI, or [$^{131}$I] KI.

In some embodiments, the methods for iodinating anti-TAG-72 imaging agents can further comprise reacting ammonia or an alkylamine, an amino acid comprising a primary amine, or a peptide comprising a primary amine with hypochlorite under conditions effective to form the chloramine. In these embodiments, the molar ratio of the ammonia or alkylamine and the hypochlorite can be from 0.8:1 to 3:1 (e.g., from 0.8:1 to 2:1, from 0.8:1 to 1.5:1, or from 0.8:1 to 1.2:1). In certain embodiments, the molar ratio of the ammonia or alkylamine and the hypochlorite can be about 1:1.

As discussed above, the methods described herein can be used to iodinate anti-TAG-72 imaging agents that include, for example, an oxidatively unstable moiety (e.g., such as an optical dye used herein as a detectable label on the anti-TAG-72 imaging agents disclosed herein) without adversely impacting the detectable label. Accordingly, in some embodiments, the anti-TAG-72 imaging agent comprising a detectable label can further comprise radiolabel, and the detectable label remains intact following the reacting step such that the iodinated anti-TAG-72 imaging agent also includes the detectable label (e.g., a group that includes a conjugated moiety).

In some embodiments, the oxidatively unstable moiety (i.e., the dectable label) can be a moiety that is detectable in the body of a subject by an imaging technique such as X-ray radiography, ultrasound, computed tomography (CT), single-photon emission computed tomography (SPECT), magnetic resonance imaging (MRI), positron emission tomography (PET), Optical Fluorescent Imaging, Optical Visible light imaging, and nuclear medicine including Cerenkov Light Imaging.

In one aspect, disclosed herein are methods of making a ®-anti-TAG-72 imaging agent comprising the formula Y-R (such as, for example, such as, for example 3E8.scFv.Cys-IR), wherein Y comprises an anti-TAG-72 binding moiety and R comprises a first detectable label; wherein ® is a radioactive labeling atom that is useful for SPECT/CT or PET/CT, a radioactive labeling atom that is useful for RADS surgical guidance, or a radiolabeling atom useful for both SPECT/CT or PET/CT and RADS said method comprising providing an anti-TAG-72 imaging agent comprising a tyrosine residue; and reacting the biomolecule with a chloramine and an iodine source under conditions effective to form an iodinated biomolecule, wherein the iodinated biomolecule comprises an iodinated tyrosine residue.

d) Immunohistochemistry

Disclosed herein are methods of using immunohistochemistry (IHC) utilizing the anti-TAG-72 imaging agents disclosed herein to detect cancer. IHC detects target molecules through antigen-antibody complexes in a pathological specimen using enzyme-linked antigens or antibodies.

A multitude of benefits are realized with IHC versus traditional immunofluorescence. For example, unlike immunofluorescence, IHC can be used with commonly used formalin-fixed paraffin-embedded tissue specimens. Pathological specimens, including histological tissue sections and/or other biological preparations such as tissue culture cells and PAP smears, are commonly used in diagnostic pathology and can be easily screened via IHC. Further. IHC staining is permanent and preserves cell morphology. A comparison of the cell morphology and antigen proliferation on two different slides can be useful in monitoring the progression of a disease.

Once a labeled antibody has been attached, either directly or indirectly, to the specimen, a substrate, specific for the enzyme, is added to the specimen. When the substrate is added, the enzyme label converts the substrate causing a color change that can be seen with light microscopy. The presence of a color change indicates the presence of the target molecule and allows an observer to determine, assess, and diagnose the disease level and severity.

e) In Vivo Imaging

The anti-TAG-72 imaging agents of the presently disclosed subject matter also are useful for in vivo imaging, wherein an antibody labeled with a detectable moiety such as a radio-opaque agent and/or a radioisotope is administered to a subject, in some embodiments via intravenous administration, and the presence and location of the labeled antibody in the host is assayed. This imaging technique can be useful in the staging and treatment of malignancies.

Therefore, disclosed is a method of in vivo treatment of cancer comprising the steps of: (a) intravenously administering a radionuclide-labeled scFv; (b) thereafter detecting tumor cells using a radionuclide activity probe; and (c) thereafter removing the detected tumor cells by surgical excision.

Thus, in some embodiments, a composition of the presently disclosed subject matter comprises a label that can be detected in vivo. The term "in viva" as used herein to describe imaging or detection methods, refers to generally non-invasive methods such as scintigraphic methods, magnetic resonance imaging, ultrasound, or fluorescence, each described briefly herein below. The term "non-invasive methods" does not exclude methods employing administration of a contrast agent to facilitate in vivo imaging.

In some embodiments, the detectable moiety can be conjugated or otherwise associated with the scFv of the presently disclosed subject matter, a therapeutic, a diagnostic agent, a drug carrier, or combinations thereof as set forth in more detail hereinabove. Following administration of the labeled composition to a subject, and after a time sufficient for binding, the biodistribution of the composition can be visualized. The term "time sufficient for binding" refers to a temporal duration that permits binding of the labeled agent to a radiation-induced target molecule.

f) Scintigraphic Imaging

Scintigraphic imaging methods include SPECT (Single Photon Emission Computed Tomography), PET (Positron Emission Tomography), gamma camera imaging, and rectilinear scanning. A gamma camera and a rectilinear scanner each represent instruments that detect radioactivity in a single plane. Most SPECT systems are based on the use of one or more gamma cameras that are rotated about the subject of analysis, and thus integrate radioactivity in more than one dimension. PET systems comprise an array of detectors in a ring that also detect radioactivity in multiple dimensions.

Imaging instruments suitable for practicing the detection and/or imaging methods of the presently disclosed subject matter, and instruction for using the same, are readily available from commercial sources. For example, a SPECT scanner can be used with a CT scanner, with coregistration of images. As in PET/CT, this allows location of tumors or tissues which may be seen on SPECT scintigraphy, but are difficult to precisely locate with regard to other anatomical structures. Both PET and SPECT systems are offered by ADAC of Milpitas, California, United States of America, and Siemens of Hoffman Estates, Illinois, United States of America. Related devices for scintigraphic imaging can also be used, such as a radio-imaging device that includes a plurality of sensors with collimating structures having a common source focus.

When scintigraphic imaging is employed, the detectable label comprises in some embodiments a radionuclide label, in some embodiments a radionuclide label selected from the group consisting of tritium, $^{99m}$Tc, $^{67}$Ga, $^{68}$Ga, $^{66}$Ga, $^{47}$Sc, $^{51}$Cr, $^{141}$Ce, $^{111}$In, $^{18}$F, $^{11}$C, $^{14}$C, $^{13}$N, $^{15}$N, $^{17}$O, $^{32}$P, $^{35}$S, $^{168}$Yb, $^{175}$Yb, $^{140}$La, $^{90}$Y, $^{88}$Y, $^{86}$Y, $^{153}$Sm, $^{166}$Ho, $^{165}$Dy, $^{166}$Dy, $^{62}$Cu, $^{64}$Cu, $^{65}$Cu, $^{67}$Cu, $^{77}$Br, $^{80m}$Br, $^{95}$Ru, $^{97}$Ru, $^{103}$Ru, $^{105}$Ru, $^{107}$Hg, $^{99m}$Re, $^{105}$Re, $^{101}$Re, $^{186}$Re, $^{188}$Re, $^{123}$I, $^{124}$I, $^{125}$I, $^{131}$I, $^{133}$I, $^{111}$In, $^{113m}$In, $^{121m}$Te, $^{122m}$Te, $^{125m}$Te, $^{165}$Tm, $^{168}$Tm, $^{167}$Tm, $^{20}$Hg, $^{203}$Pb, $^{211}$Bi, $^{212}$Bi, $^{213}$Bi $^{214}$Bi, $^{225}$Ac, $^{210}$At, $^{210}$At, $^{211}$At, $^{105}$Rh, $^{109}$Pd, $^{117m}$Sn, $^{149}$Pm, $^{153}$Sm $^{161}$Tb, $^{177}$Lu, $^{198}$Au, $^{199}$Au, $^{89}$Zr, and nitride or oxide forms derived there from. In some embodiments, the radionuclide label comprises $^{131}$I or $^{99m}$Tc.

Methods for radionuclide labeling of a molecule so as to be used in accordance with the disclosed methods are known in the art. For example, a targeting molecule can be derivatized so that a radioisotope can be bound directly to it. Alternatively, a linker can be added that to enable conjugation. Representative linkers include diethylenetriamine pentaacetate (DTPA)-isothiocyanate, succinimidyl 6-hydrazinium nicotinate hydrochloride (SHNH), and hexamethylpropylene amine oxime (U.S. Pat. No. 6,024, 938). Additional methods can be found in U.S. Pat. No. 6,080,384.

When the labeling moiety is a radionuclide, stabilizers to prevent or minimize radiolytic damage, such as ascorbic acid, gentisic acid, or other appropriate antioxidants, can be added to the composition comprising the labeled targeting molecule.

g) Ultrasound

Ultrasound imaging can be used to obtain quantitative and structural information of a target tissue, including a tumor with the anti-TAG-72 imaging agents described herein when administered intraparitoneally otherwise the particles are too large to exit the blood. Administration of a contrast agent, such as gas microbubbles, can enhance visualization of the target tissue during an ultrasound examination. In some embodiments, the contrast agent can be selectively targeted to the target tissue of interest, for example by using a peptide for guided drug delivery (e.g., radiation guided drug delivery) as disclosed herein. Representative agents for providing microbubbles in vivo include but are not limited to gas-filled lipophilic or lipid-based bubbles (e.g., U.S. Pat. Nos. 6,245, 318; 6,231,834; 6,221,018; and 5,088,499). In addition, gas or liquid can be entrapped in porous inorganic particles that facilitate microbubble release upon delivery to a subject (U.S. Pat. Nos. 6,254,852 and 5,147,631).

Gases, liquids, and combinations thereof suitable for use with the presently disclosed subject matter include air; nitrogen; oxygen; is carbon dioxide; hydrogen; nitrous oxide; an inert gas such as helium, argon, xenon or krypton; a sulfur fluoride such as sulfur hexafluoride, disulfur decafluoride or trifluoromethylsulfur pentafluoride; selenium hexafluoride; an optionally halogenated silane such as tetramethylsilane; a low molecular weight hydrocarbon (e.g. containing up to 7 carbon atoms), for example an alkane such as methane, ethane, a propane, a butane or a pentane, a cycloalkane such as cyclobutane or cyclopentane, an alkene such as propene or a butene, or an alkyne such as acetylene; an ether; a ketone; an ester; a halogenated low molecular weight hydrocarbon (e.g. containing up to 7 carbon atoms); or a mixture of any of the foregoing. Halogenated hydrocarbon gases can show extended longevity, and thus are preferred for some applications. Representative gases of this group include decafluorobutane, octafluorocyclobutane, decafluoroisobutane, octafluoropropane, octafluorocyclopropane, dodecafluoropentane, decafluorocyclopentane, decafluoroisopentane, perfluoropexane, perfluorocyclohexane, perfluoroisohexane, sulfur hexafluoride, and perfluorooctaines, perfluorononanes; perfluorodecanes, optionally brominated.

Attachment of targeting ligands to lipophilic bubbles can be accomplished via chemical crosslinking agents in accordance with standard protein-polymer or protein-lipid attachment methods (e.g., via carbodiimide (EDC) or thiopropionate (SPDP)). To improve targeting efficiency, large gas-filled bubbles can be coupled to a targeting ligand using a flexible spacer arm, such as a branched or linear synthetic polymer (U.S. Pat. No. 6,245,318). A targeting ligand can be attached to the porous inorganic particles by coating, adsorbing, layering, or reacting the outside surface of the particle with the targeting ligand (U.S. Pat. No. 6,254,852).

h) Fluorescence Imaging

Non-invasive imaging methods can also comprise detection of a fluorescent label. A drug comprising a lipophilic component (therapeutic agent, diagnostic agent, vector, or drug carrier) can be labeled with any one of a variety of lipophilic dyes that are suitable for in vivo imaging. Representative labels include but are not limited to carbocyanine and aminostyryl dyes, preferably long chain dialkyl carbocyanines (e.g. Dil, DiO, and DiD available from Molecular Probes Inc. of Eugene, Oregon, United States of America) and dialkylaminostyryl dyes. Lipophilic fluorescent labels can be incorporated using methods known to one of skill in the art. For example VYBRANT™ cell labeling solutions are effective for labeling of cultured cells of other lipophilic components (Molecular Probes Inc. of Eugene, Oregon, United States of America).

A fluorescent label can also comprise sulfonated cyanine dyes, including Cy5.5 and Cy5 (available from Amersham of Arlington Heights, Illinois, United States of America). IRD41 and IRD700 (available from Li-Cor, Inc. of Lincoln, Nebraska), NIR-1 (available from Dejindo of Kumamoto, Japan), and LaJolla Blue.

In addition, a fluorescent label can comprise an organic chelate derived from lanthanide ions, for example fluorescent chelates of terbium and europium (U.S. Pat. No. 5,928,627). Such labels can be conjugated or covalently linked to a drug as disclosed therein.

For in vivo detection of a fluorescent label, an image is created using emission and absorbance spectra that are appropriate for the particular label used. The image can be visualized, for example, by diffuse optical spectroscopy. Additional methods and imaging systems are described in U.S. Pat. Nos. 5,865,754; 6,083,486; and 6,246,901, among other places.

i) Radioimmunoguided System® (RIGS)

Another preferred application of the anti-TAG-72 imaging agents is in the Radioimmunoguided System®. This technique, also known as the RIGS® System involves the intravenous administration of a radiolabeled monoclonal antibody or its fragment prior to surgery. After allowing for tumor uptake and blood clearance of radioactivity, the patient is taken to the operating room where surgical exploration is effected with the aid of a hand-held gamma activity probe, e.g., Neoprobe®1000. This helps the surgeon identify the tumor metastases and improve the complications of excision. The RIGS® system is advantageous because it allows for the detection of tumors not otherwise detectable by visual inspection and/or palpation. See, O'Dwyer et al, Arch. Surg., 121:1 391-1394 (1986). This technique is described in detail in Hinkle et al, Antibody, Immunoconjugates and Radiopharmaceuticals, 4:(3)339-358 (1991) (citing numerous references describing this technique). This reference also discloses the use of this technique with the CC49 monoclonal antibody itself. This technique is particularly useful for cancers of the colon, breast, pancreas, and ovaries.

In some embodiments, the anti-TAG-72 imaging agents of the presently disclosed subject matter are employed for in vivo imaging of tumors, wherein a composition of the presently disclosed subject matter that has been labeled with an imaging moiety such as a radio-opaque agent, a radioisotope, or other imaging agent is administered to a subject, and the presence and location of the detectibly-labeled composition in the subject is assayed. This imaging technique can be useful in the staging and treatment of malignancies. In some embodiments, an antibody is labeled with any moiety that is detectable in situ in a subject, for example by nuclear magnetic resonance, radiology, or other detection methods known in the art.

As such, the presently disclosed subject matter also provides methods for detecting tumors in subjects. In some embodiments, the presently disclosed methods comprise (a) administering to the subject a composition comprising the scFv of the presently disclosed subject matter conjugated to a detectable label; and (b) detecting the detectable label to thereby detect the tumor.

5. Methods for Predicting the Recurrence and/or Progression of Cancer in a Subject In some embodiments, the presently disclosed subject matter also provides methods for predicting the recurrence of cancer in a subject. In some embodiments, the methods comprise (a) isolating a biological sample comprising cells from a subject with a cancer; (b) contacting the biological sample with scFv of the presently disclosed subject matter; and (c) identifying in the biological sample one or more cells that bind to the scFv of the presently disclosed subject matter, whereby the recurrence of a cancer is predicted in the subject. With respect to these methods, the identification of cells that bind to the anti-TAG-72 imaging agents of the presently disclosed subject matter can be indicative of a recurrence of a subject's cancer when the subject had previously been negative for such circulating cells. In some embodiments, the presence of cells that bind to the one or more of the antibody fragments of the presently disclosed subject matter indicates that the subject is at enhanced risk of metastatic disease relative to a subject that is negative for such cells.

6. Methods for Prognosing Progression of Cancer

The presently disclosed subject matter also provides methods for prognosing progression of a cancer in subjects. In some embodiments, the methods comprise isolating a biological sample comprising cells from a subject with a cancer; contacting the biological sample with the scFv of the presently disclosed subject matter under conditions sufficient for the scFv to bind to an epitope present on a tumor and/or a cancer cell, if present, in the biological sample; and identifying in the biological sample one or more cells that bind to the scFv, whereby progression of a cancer is prognosed in the subject. In some embodiments, the biological sample comprises a blood sample, a lymph sample, or a fraction thereof. In some embodiments, the cancer is a adenocarcinoma or colon cancer.

As used herein, the phrase "prognosing progression of a cancer" refers to evaluating indicia of a cancer disease at a given time point and comparing the same to the indicia of the cancer disease taken at an earlier time point, wherein the comparison is indicative of a progression of the cancer in the subject. In some embodiments, progression of the cancer comprises metastasis of the cancer in the subject.

7. Other Uses

The antibodies of the presently disclosed subject matter can also be employed in various assay methods, such as but not limited to competitive binding assays, direct and indirect sandwich assays, and immunoprecipitation assays (see e.g., Zola, 1987; Harlow & Lane, 1988).

The antibodies of the presently disclosed subject matter also are useful as affinity purification agents. In this process, one or more antibodies are immobilized on a suitable support (such as, but not limited to a Sephadex resin or filter paper) using methods well known in the art. See e.g., Harlow & Lane, 1988.

8. Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews*, 129:57-80, (1992); and Roffler, et al., *Biochem. Pharmacol*, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214-6220. (1989); and Litzinger and Huang, *Biochimica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

a) Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, PA 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

Effective dosages and schedules for administering the compositions may be determined empirically, and making such determinations is within the skill in the art. The dosage ranges for the administration of the compositions are those large enough to produce the desired effect in which the symptoms of the disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counter indications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., *Handbook of Monoclonal Antibodies*, Ferrone et al., eds., Noges Publications, Park Ridge, N.J., (1985) ch. 22 and pp. 303-357; Smith et al., *Antibodies in Human Diagnosis and Therapy*, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

D. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1: Materials and Methods

Human TAG-72 antigen was purchased from Sigma (Saint Louis, MO, USA). Amicon Ultra-0.5 Centrifugal filter units were purchased from Millipore (Billerica, MA, USA). IRDye800-maleimide was purchased from Li-COR, Inc. (Lincoln, NE, USA). The 3E8ΔCH2 was manufactured by Catalent Pharma Solution (Middleton. WI, USA), according to the method established by Slavin-Chiorini. The 3E8 binding sequence for 3E8.scFv.Cys was identical in the two 3E8 proteins, as listed in Magliery.
a) Cell Line LS-174T cells were obtained from ATCC (Manassas. VA, USA) and grown in McCoy's 5A medium in addition to 10% of bovine serum (FBS, Atlanta Biologicals, Awreneville, GA, USA) and 1% of penicillin-streptomycin (Invitrogen Life Technologies, Carlsbad, CA, USA), at 37° C. in a humidified atmosphere containing 5% $CO_2$. All cell incubations were done in the incubator under these conditions. Quantitative data are reported as the mean, with uncertainty as the standard deviation (SD).
b) In Vitro Binding Studies The human adenocarcinoma cell line, LS-174T, expresses and secretes TAG-72. To verify the TAG-72 binding specificity of 3E8.scFv.Cys-IR800 conjugate, we ran a blocking experiment. LS-174T cells ($1 \times 10^5$ cells per well) were cultured in a 96-well plate 16 h prior to the binding assay. The cells were incubated with 100 µl of serum-free growth medium containing 7.5 µM 3E8ΔCH2 for 3 h and then washed twice with PBS to remove the unbound 3E8ΔCH2. 150 µmol of 3E8.scFv.Cys-IR800 was then added to these cells in 100 µl of serum-free growth medium. At the same time control cells not exposed to 3E8ΔCH2 were treated with varying concentrations of 3E8.scFv.Cys-IR800: 1.5 µM, 0.75 µM, and 0.375 µM, each in 100 µl. All treated cells were incubated for 3 h, then washed 5 times with 200 µl of PBS. 60 µl of PBS were then added to all wells on the plate for measurement of the fluorescence intensity at (764 nm ex, 809 nm em) nm in a Synergy H4 hybrid multi-mode microplate reader (BioTek, Winnoski, VT, USA).
c) In Vivo Tumor Model The animal experiments were performed under a protocol approved by The Ohio State University Institutional Animal Care and Use Committee. All of the guidelines were followed including euthanization of animals in obvious distress. The orthotopic LS-174T tumor model creation was patterned after a published method. Five-six week-old female athymic nu/nu mice (Charles River Laboratories, MA) were injected intraperitoneal (i.p.) with $6 \times 10^6$ LS-174T cells in 600 µl of PBS. Due to the small size of the of orthotopic tumors, palpation was not possible, and tumor progress was assessed by body weight and general physical condition changes, which were monitored three times per week. Through experimentation, it was found that the implanted LS-174T cells required 12-14 days to produce tumors clearly visible by eye at necropsy.
d) Pharmacokinetics Studies Non tumor bearing female BALB/c mice (N=4) were injected under isoflurane anesthesia with 2 nmol 3E8.scFv.Cys-IR800 in 100 µl PBS via tail vein to perform pharmacokinetics studies. Mice remained conscious except during the blood draws. The blood was collected at 1 min, 0.5, 1, 2, 4, 8 and 24 h post-injection, 5 µl of blood being collected from the saphenous vein and loaded into a black wall 96-well plate containing 95 µl PBS buffer with 0.15% EDTA (pH 8.5) and 0.2% BSA per well. The mouse blood volume was calculated as 78 ml/kg mouse. Blood and urine samples from an uninjected mouse were used as negative controls, 0% ID (Injected Dose), and 100% ID standards. The fluorescence intensity was measured with the Synergy H4 microplate reader recording NIRF signal above 800 nm.
e) Near Infrared Fluorescence In Vivo Imaging Imaging experiments performed in the LS-174T tumor-bearing mice used 1 nmol of 3E8.scFv.Cys-IR800 administered i.p. into N=4 conscious mice, and N=3 mice were sham injected (PBS containing no 3E8.scFv.Cys-IR800). Six tumor bearing mice were used for the blocking experiment. Mice in the blocked imaging group (N=3) were injected i.p with 10 nmol of 3E8ΔCH2, and then 3 h later, with 1 nmol 3E8.scFv.Cys-IR800. These were compared with N=2 mice injected only with 1 nmol 3E8.scFv.Cys-IR800 and N=2 mice that were sham injected. All animals were euthanized at 24-h post-administration and the abdomen was opened immediately for imaging using a laser excitation Fluobeam™ 800 NIR imaging system (Fluoptics, Grenoble, France). The Fluobeam system excites with a 780-nm emission laser and records with a CCD camera with >800 nm emission filtering.

2. Example 2: Engineered 3E8.scFv.Cys Antibody Fragment

The 3E8.scFv was constructed with the intention of creating a low molecular weight protein that retained high specificity for targeting to TAG-72. 3E8.scFv.Cys was expressed in a Walker series C43 *E. coli* from the overexpression plasmid, pHLIC. Transformants were escalated to a larger scale of growth through standard techniques. After cells were lysed with an Emulsiflex, the supernatant was purified through a GE Healthcare HiTrap Protein L column and a cation exchange chromatography Resource S column.

Figure 2:
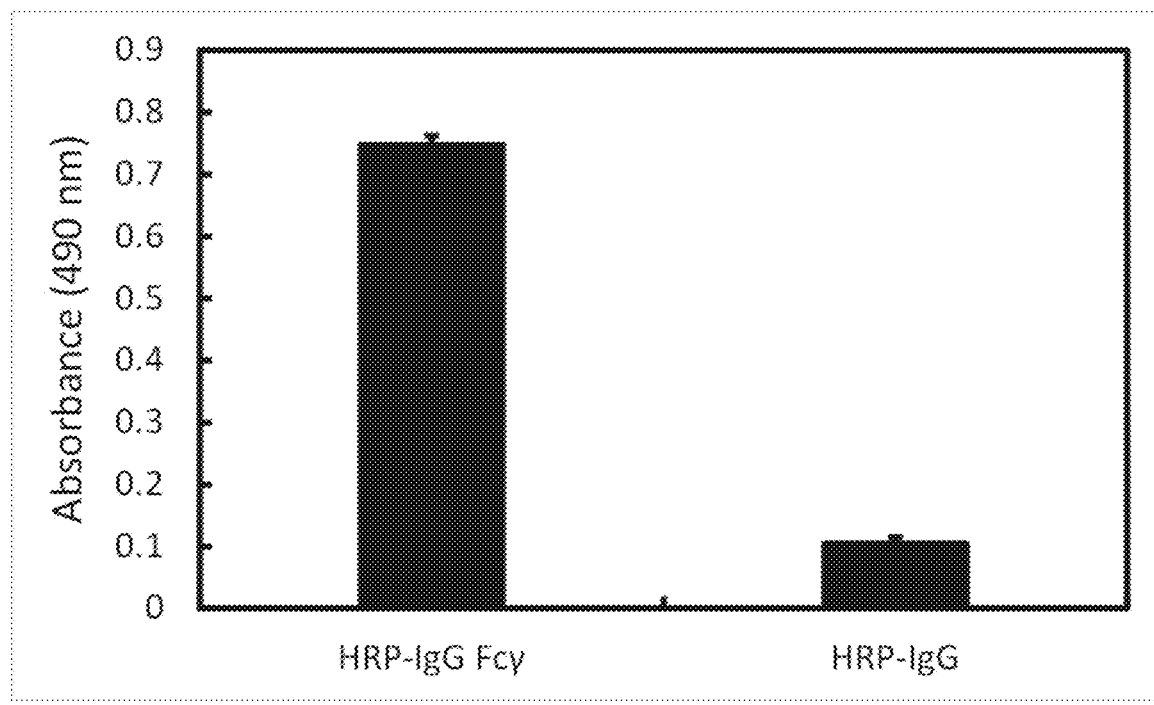
FIG. 2 shows validation of 3E8ΔCH2 binding by HRP ELISA on a Bovine Submaxillary Mucine (BSM) coated substrate.

A dot blot assay showed that the 3E8.scFv.Cys fragment binds to BSM (bovine submaxillary mucin, Type I-S. Sigma-Aldrich. St. Louis, MO) which contains sialy-Tn. We validated the binding specificity of 3E8ΔCH2 to TAG-72 by an indirect ELISA (FIG. 2). Briefly, a two-step ELISA was applied to detect the absorbance using a plate reader described below. Primary antibody was first bound to the TAG-72 antigen coated 96-well microplates, and then incubated with labeled secondary antibody HRP-IgG Fcγ (Peroxidase-conjugated AffiniPure Goat Anti-Human IgG, Fcγ Fragment Specific, Jackson ImmunoResearch, Inc., West Grove, PA, USA), then absorbance was read at 490 nm. The binding constants of 3E8ΔCH2 and 3E8.scFv.Cys to BSM-coated plates were determined by Surface Plasmon Resonance (SPR) using a GE Health Sciences Biacore T100 system, calculating KD from the quotient of the measured rate constants, koff/kon (FIG. 3).

3. Example 3: 3E8.scFv.Cys-IR800 Synthesis and Analytical Confirmation

The 3E8.scFv.Cys-IR800 conjugate was synthesized using an optimized maleimide conjugation protocol. A total volume of 100 μl of a PBS solution containing 200 μg (7.14 nmol) of 3E8.scFv.Cys was prepared and reacted with 1.8 μL of 10 mM IRDye800-maleimide (1:2.5 3E8.scFv.Cys:IRDye800-maleimide mole ratio) that was gradually added to the 3E8.scFv.Cys solution with gentle vortexing, followed by shaking the reaction tube on an arm shaker for 3 h at room temperature in the dark. The solution was loaded onto an Amicon Ultra-0.5 centrifugal filter unit to remove excess IRDye800-maleimide and concentrate the product. The filter was washed twice with PBS. Then the solution above the 10 kDa cutoff filter was collected.

Linear mode ultrafleXtreme MALDI-TOF/TOF (Bruker, UK) was run (sinapinic acid was used as the matrix) to verify the identity of the product. Size exclusion column HPLC (LC-10ATVPT, Shimadzu, Columbia, MD; column: Agilent Bio SEC-3 column 3 μm. 100 angstrom, 4.6×30 cm) run in PBS with an 800 nm fluorescence detector (Shimadzu RF-10AXL) was used to determine purity of the primary product seen in the mass spectrum. The biological functionality of 3E8.scFv.Cys-IR800 was validated by applying the indirect ELISA method as above.

Figure 1:
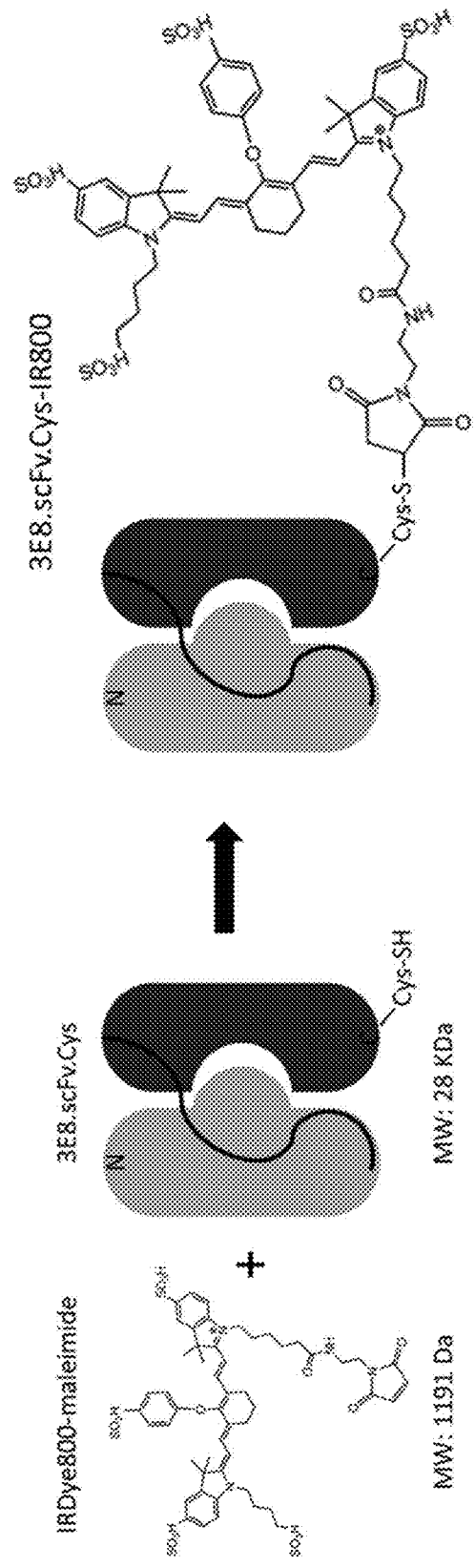
FIG. 1 shows synthesis and structure of 3E8.scFv.Cys-IR800.

Discussion of Example 1. The 3E8.scFv.Cys fragment was created by protein engineering based on the full-length sequence of the humanized 3E8 antibody. FIG. 1 shows the structures of the components of the final product, 3E8.scFv.Cys-IR800. The mass spectrum confirmed the identity of 3E8.scFv.Cys-IR800 as shown in FIG. 4. The mass spectral results of several syntheses varying the dye to protein mole ratio up to 10 indicated that the reaction of 2.5 moles of IRDye800-maleimide with 1 mole of protein produced the most 1:1 conjugate. The fluorescence detected HPLC shown in FIG. 5 and showed that a greater than 90% 3E8.scFv.Cys purity of the 1:1 conjugate was achieved, with about 10% of free IRDye-800-maleimide. The 800 nm fluorescence intensity of 3E8.scFv.Cys-IR800 was found to be 39±18% diminished compared to IR800-maleimide, using a fluorescence detected concentration series measured between 0.2 and 1.0 μM protein. The conditions used allowed for the first time a 1:1 formulation to be made at very high 90% NIRF purity.

4. Example 4: In Vitro Binding Studies of 3E8.scFv.Cys-IR800

The binding constant of 3E8.scFv.Cys was 12 nM, compared to 13.6 nM for the bivalent fragment, 3E8ΔCH2 (FIG. 3). FIGS. 6 and 7 demonstrate concentration dependent binding of 3E8.scFv.Cys-IR800 to TAG-72 on TAG-72 coated plates (FIG. 6) and on LS-174T human colon cancer cells expressing TAG-72 (FIG. 7). Binding was proportional to the concentration of 3E8.scFv.Cys-IR800 in the incubation media, measured after equivalent durations of incubations. 3E8ΔCH2 binds to the same epitope on TAG-72, so a five-fold excess concentration of 3E8ΔCH2 was used as a blocking reagent to confirm the specific binding of 3E8.scFv.Cys-IR800 to TAG-72 on LS-174T cells. 7.5 μM of non-fluorescent 3E8ΔCH2 blocked the binding of 1.5 μM 3E8.scFv.Cys-IR800, as shown in FIG. 7. This latter experiment demonstrates the TAG-72 specific nature of the binding of 3E8.scFv.Cys-IR800 to the cells.

The SPR data in FIG. 3 demonstrated that very strong binding (Kd=12 nM) to plated TAG-72 was maintained after the protein modification to make 3E8.scFv.Cys-IR800.

5. Example 5: Pharmacokinetics

Blood concentration vs. time curves for the 3E8.scFv.Cys-IR800 in non-tumor bearing mice are shown in FIG. 8. Treating the blood clearance as bimodal, the first three points yielded a half-time of ~30 minutes for distribution ($r^2$=0.974) and the last three points yielded an elimination halftime of 10 h ($r^2$=0.997), based on linear log % ID vs. time fits. Urinary excretion was obvious from a brightened bladder on fluorescent images and 26% of the administered agent was recovered in urine after only the first 3 h. The 3E8.scFv.Cys-IR800 cleared the blood very rapidly compared to the published Cy7-3E8ΔCH2 antibody fragment (120 kDa; T½=3-5 h) and Cy7-CC49 antibody (220 kDa; T½=61.2 h).

6. Example 6: In Vivo Imaging

Tumor deposits in the peritoneal cavity were observed 12-14 days after i.p. inoculation. Most of the tumor deposits were small (1-3 mm in diameter) and located mainly in the upper abdomen in the liver hilum, the greater omentum and adjacent to the spleen (FIG. 9, right side). H&E staining shown in FIG. 10 validated the identification of the growths in FIG. 9 as tumors. Based on previous experience and pilot studies, 24 h post administration was chosen as the imaging window in the tumor bearing mice. FIG. 9 (left side) shows one tumor bearing mouse imaged with 1 nmol i.p. administration of 3E8.scFv.Cys-IR800 compared to a barely visible control mouse that was sham injected. The photographs of these two mice are shown in the panel to the right of the NIRF images. The NIRF images clearly demonstrate that the 3E8.scFv.Cys-IR800 binds to and allows brightly contrasted NIRF imaging of the tumors, even against the liver background.

To demonstrate receptor specificity, in another group of tumor bearing mice, 10 nmol of 3E8ΔCH2 (with no NIRF label) was administered i.p. 3 h prior to i.p. administration of 1 nmol 3E8.scFv.Cys-IR800. The administered 3E8ΔCH2 binds to TAG-72 targets and prevents the binding later on of the 3E8.scFv.Cys-IR800. FIG. 5 shows that 3E8ΔCH2 successfully blocked 3E8.scFv.Cys-IR800 binding to the LS-174T tumors, which conclusively demonstrates the binding specificity of 3E8.scFv.Cys-IR800. This is demonstrated in FIG. 11.

FIG. 12 demonstrates the surprising advantage of using an ip administration over an iv administration when using the novel 3E8.scFv.Cys-IR800 to guide colon cancer surgery. 1 nmol administered i.v. showed some fluorescence intensity in tumors while i.p administration of 1 nmol 3E8.scFv.Cys-IR800 showed higher intensity and better highlighted tumors. With iv administration, the tumors were less intensity NIRF compared to the liver, but in the ip administration, the tumors had greater intensity compared to the liver.

7. Example 7: Discussion of the Examples

Orthotopic LS-174T tumor biodistributions of LS-174T targeted immunoconjugates were tested in a biodistribution of a radiolabeled anti-CEA antibody, i.p. and i.v. administration routes were compared. The i.p. route produced 25% higher tumor uptake, but this prior art showed no differences in organ uptakes at 24 h post administration. Surprisingly, it was found that the i.p. route for the tumor imaging of 3E8.scFv.Cys-IR800, in opposition to the prior art teaching, produced a greatly attenuated liver signal and greater tumor to liver background ration, that is particularly useful in colon cancer surgery where metastases are most often found located in the liver.

A utility of this invention are site specifically labelled molecule, 3E8.scFv.Cys-IR800. A further utility is the use of these new entities with i.p. administration. Site specific labeling by the maleimide dye resulted in a discrete, 1 protein: 1 dye conjugate of high purity, that maintains specific target binding in vitro and in vivo. A further utility of this invention is described in FIG. 13 and is the use the 3E8.scFv.Cys-IR800 in combination with the highly sensitive, small FOV RADS technology, by radiolabeling ® the 3E8.scFv.Cys-IR800 making ®-3E8.scFv-IR800. Combination of the rapid and wide field view of OSN with ®-3E8.scFv-IR800 or 3E8.scFv.Cys-IR800 with the highest sensitivity detection using the ® label for RADS, after resecting the tumor under OSN, detects any tiny remaining cancer that can then be further resected. The slowness disadvantage of the RADS is thus overcome by using the OSN NIRF to establish a smaller filed of view in which to use RADS, thus combining the advantages and disadvantages of OSN NIRF and RADS to create a powerful new process with the speed of OSN NIRF and the sensitivity of detection of RADS.

A further utility is the overall process of treating the TAG-72 positive colon cancer patient, as described in FIG. 13. An in vitro test of the biopsy specimen, followed by TAG-72 specific PET/CT can be used to select surgical candidates. Then simultaneously applied TAG-72 OSN plus RADS detecting the $^{89}Zr$ or $^{124}I$ or other ® labeled TAG-72 binding entity either as two separate entities or as a dual probe can guide potentially curative surgery on this well selected population, avoiding the common finding of unexpected extensive disease that requires immediate termination of the surgery. It will be obvious to one skilled in the art that other dyes that have NIRF emissions above 800 nm can also be useful as long as they contain a maleimide group or other group specific to reaction with cysteine. It can also be useful that the ® labeled PET/CT agent can also be the RADS agent. Further the three functions of RADS, PET/CT and NIRF agent can be combined in a single agent, two agents or three separate agents each with a different separate function.

Dicyanine dyes that are useful in this invention include IRdye800. AlexaFluor 790, ZW-800 (Frangioni et al), Indocyanine Green, S0456, and the like, provided their emission peak is at least 790 nm and preferably greater than 790 nm, most preferably separated from the absorption peak by more than 15 nm, most preferably 19-35 nm, and that primarily the emitted fluorescent light is above 800 nm.

8. Example 8: Radiolabeling of Tyrosine Residues Using Chloramines a) Preparation of Mono Chloramine from Ammonium Hydroxide and Sodium Hypochlorite Stock solutions of sodium hypochlorite and ammonium hydroxide can be prepared by diluting concentrated solutions of the two reagents as received. The concentration of the diluted sodium hypochlorite solution can be determined by measured absorbance of the solution at 294 nm and extinction coefficient ($350\ M^{-1}\ cm^{-1}$). Five milliliters of sodium hypochlorite solution (8.1 mM) can be added dropwise to five milliliters of stirred solution of ammonium hydroxide (10 mM) in a beaker to form a solution of mono chloramine ($NH_2Cl$). The concentration of the mono chloramine solution can be determined from the measured absorbance of the solution at 244 nm and extinction coefficient ($461\ M^{-1}cm^{-1}$) and the $NH_2Cl$ solution can be used for non-radioactive and radio labeling of tyrosine, peptides, and proteins.

b) $^{125}I$ Labeling of Tyrosine

A known amount of tyrosine amino acid (1.05 μmole) in PBS (pH7.4) can be added to a 1.5 mL polypropylene tube containing 0.5 mL phosphate buffer (0.1 M. pH 7.4). Career free $^{125}INa$ (~50 μCi) followed by 1.5 μmole mono chloramine solution in phosphate buffer can be added to the tube. The reaction mixture can be agitated and mixed with the pipette after each addition of the reagents. The reaction mixture van be incubated at room temperature for 15 minutes. The radiolabeling reaction can be quenched by addition of 0.125 mL of 10 mM sodium bisulfite solution in PBS (pH 7.4). Unreacted $^{125}INaI$ can be removed from the reaction mixture by using a conditioned Sep-Pak Cis Light cartridge. The cartridge can be washed with 1.5 mL water and followed by eluting with several 100 μL portions of ethanol. Each fraction can be analyzed for total radioactivity by a dose calibrator. Efficiency of radiolabeling can be calculated as 100%. The sample containing most of the activity can be analyzed by using a RP-HPLC method. Two peaks at retention times 10.1 (7.7%) and 18.6 (92.3%) minutes can be observed by the radioisotope detector.

c) $^{125}I$ Radiolabeling of a Antibody Fragment, 3E8.scFv.Cys

An antibody fragment (3E8.scFv.Cys) can be radiolabeled with $^{125}I$ as taught in PCT Application No. US2017/059503, filed on Nov. 1, 2017 and U.S. Provisional Application No. 62/415,871, filed on Nov. 1, 2016, applications which are incorporated herein by reference in their entirety for their teachings of iodination of biomolecules. A 50 μg of the antibody fragment, 3E8.scFv.Cys, can be transferred into an Eppendorf tube containing 100 μL of sodium phosphate buffer (0.1 M pH 7.4). Career free $^{125}INa$ (~113 μCi) followed by mono chloramine (0.8 μmole) in phosphate buffer (pH 7.4) can be added to the tube. The reaction mixture can be agitated and mixed with the pipette after addition of each reagent. The reaction mixture can be incubated at room temperature for 10 min and the reaction can be quenched by adding 100 uL of 10 mM Sodium Bisulfite. The crude reaction mixture can be purified using a conditioned Sephadex G-25 or PD-10 column. The purified material can be analyzed by a paper chromatographic method for the presence of free $^{125}$I.

E. References

Adumeau P. Sharma S K, Brent C, Zeglis B M. Site-Specifically Labeled Immunoconjugates for Molecular Imaging-Part 1: Cysteine Residues and Glycans. Mol Imaging Biol. 2016; 18(1):1-17.

Adumeau P, Sharma S K, Brent C, Zeglis B M. Site-Specifically Labeled Immunoconjugates for Molecular Imaging-Part 2: Peptide Tags and Unnatural Amino Acids. Mol Imaging Biol. 2016; 18(2):153-65.

Altman P L. Blood and other body fluids. New York, NY: Macmillan Co; 1954.

Antoniou S A, Antoniou G A, Koch O O, Pointner R, Granderath F A. Robot-assisted laparoscopic surgery of the colon and rectum. Surg Endosc. 2012:26(1):1-11.

Boonstra M C, van Driel P B A A, van Willigen D M, Stammes M A, Prevoo H A J M, Tummers Q R J G, et al. uPAR-targeted multimodal tracer for pre- and intraoperative imaging in cancer surgery. Oncotarget. 2015; 6(16): 14260-73.

Boonstra M C, Verspaget H W, Ganesh S, Kubben F J G M, Vahrmeijer A L, de Velde C J H V, et al. Clinical Applications of the Urokinase Receptor (uPAR) for Cancer Patients. Curr Pharm Des. 2011; 17(19):1890-910.

Ding H M, Carlton M M, Povoski S P, Milum K, Kumar K, Kothandaraman S, et al. Site Specific Discrete PEGylation of I-124-Labeled mCC49 Fab' Fragments Improves Tumor MicroPET/CT Imaging in Mice. Bioconjug Chem. 2013; 24(11):1945-54.

Frangioni J V. In vivo near-infrared fluorescence imaging. Curr Opin Chem Biol. 2003; 7(5):626-34.

Fu X Y, Besterman J M, Monosov A, Hoffman R M. Models of human metastatic colon cancer in nude mice orthotopically constructed by using histologically intact patient specimens. Proc Natl Acad Sci USA. 1991; 88(20):9345-9.

Hermanson G T. Discrete PEG Reagents. Bioconjugate Techniques, 2nd edition. 2nd Edition ed. USA: Elsevier; 2008, p. 732-3.

Hiroshima Y, Maawy A, Metildi C A, Zhang Y. Uehara F, Miwa S, et al. Successful Fluorescence-Guided Surgery on Human Colon Cancer Patient-Derived Orthotopic Xenograft Mouse Models Using a Fluorophore-Conjugated Anti-CEA Antibody and a Portable Imaging System. Journal of Laparoendoscopic & Advanced Surgical Techniques. 2014; 24(4):241-7.

Horton K M, Abrams R A, Fishman E K. Spiral CT of colon cancer: Imaging features and role in management. Radiographics. 2000; 20(2):419-30.

Johnson V G, Schlom J, Paterson A J, Bennett J, Magnani J L, Colcher D. Analysis of a human tumor-associated glycoprotein (TAG-72) identified by monoclonal antibody B72.3. Cancer Res. 1986; 46(2):850-7.

Kinkel K, Lu Y, Both M, Warren R S, Thoeni R F. Detection of hepatic metastases from cancers of the gastrointestinal tract by using noninvasive imaging methods (US, CT, MR imaging, PET); A meta-analysis. Radiology. 2002:224(3): 748-56.

Koppe M J, Soede A C, Pels W. Oyen W J. Goldenberg D M, Bleichrodt R P, et al. Experimental radioimmunotherapy of small peritoneal metastases of colorectal origin. Int J Cancer. 2003; 106(6):965-72.

Kosaka N, Ogawa M, Choyke P L, Kobayashi H. Clinical implications of near-infrared fluorescence imaging in cancer. Future Oncology. 2009:5(9):1501-11.

Kuhry E. Schwenk W, Gaupset R, Romild U, Bonjer J. Long-term outcome of laparoscopic surgery for colorectal cancer: a cochrane systematic review of randomised controlled trials. Cancer Treat Rev. 2008:34(6):498-504.

Loy T S, Nashelsky M B. Reactivity of B72.3 with adenocarcinomas. An immunohistochemical study of 476 cases. Cancer. 1993; 72(8):2495-8.

Maawy A A, Hiroshima Y, Zhang Y, Luiken G A, Hoffman R M, Bouvet M. Polyethylene Glycol (PEG) Linked to Near Infrared (NIR) Dyes Conjugated to Chimeric Anti-Carcinoembryonic Antigen (CEA) Antibody Enhances Imaging of Liver Metastases in a Nude-Mouse Model of Human Colon Cancer. PLoS One. 2014; 9(5).

Magliery T J, Sullivan B J, Allen H C, Martin E W, Hitchcock C L, Alten E D, et al. Methods and compositions related to single chain antibody fragments that bind to tumor-associated glycoprotein 72 (tag-72). USPTO; 2014.

Mori A, Arii S. Furutani M. Mizumoto M, Uchida S, Furuyama H, et al. Soluble Flt-1 gene therapy for peritoneal metastases using HVJ-cationic liposomes. Gene Ther. 2000:7(12):1027-33.

Nayak T K, Garmestani K, Milenic D E, Brechbiel M W. PET and MRI of metastatic peritoneal and pulmonary colorectal cancer in mice with human epidermal growth factor receptor 1-targeted 89Zr-labeled panitumumab. J Nucl Med. 2012; 53(1):113-20.

Park J Y, Murakami T, Lee J Y, Zhang Y. Hoffman R M, Bouvet M. Fluorescent-Antibody Targeting of Insulin-Like Growth Factor-1 Receptor Visualizes Metastatic Human Colon Cancer in Orthotopic Mouse Models. PLoS One. 2016; 11(1).

Povoski S P, Hatzaras I S, Mojzisik C M, Arnold M W, Hinkle G H, Hitchcock C L, et al. Antigen-directed cancer surgery for primary colorectal cancer: 15-year survival analysis. Annals of surgical oncology. 2012:19(1):131-8.

Povoski S P, Hatzaras I S, Mojzisik C M, Arnold M W, Hinkle G H, Hitchcock C L, et al. Antigen-directed cancer surgery for primary colorectal cancer: 15-year survival analysis. Ann Surg Oncol. 2012; 19(1):131-8.

Povoski S P, Neff R L, Mojzisik C M, O'Malley D M, Hinkle G H, Hall N C, et al. A comprehensive overview of radioguided surgery using gamma detection probe technology. World J Surg Oncol. 2009:7:11.

Reza M M, Blasco J A, Andradas E, Cantero R, Mayol J. Systematic review of laparoscopic versus open surgery for colorectal cancer. Br J Surg. 2006:93(8):921-8.

Rijpkema M. Oyen W J. Bos D, Franssen G M, Goldenberg D M, Boerman O C. SPECT- and Fluorescence Image-Guided Surgery Using a Dual-Labeled Carcinoembryonic Antigen-Targeting Antibody. J Nucl Med. 2014; 55(9): 1519-24.

Rogers B E, Roberson P L, Shen S. Khazaeli M B, Carpenter M. Yokoyama S. et al. Intraperitoneal radioimmunotherapy with a humanized anti-TAG-72(CC49) antibody with a deleted CH2 region. Cancer Biother Radiopharm. 2005:20(5):502-13.

Rosenthal E L, Warram J M, de Boer E, Basilion J P, Biel M A, Bogyo M, et al. Successful Translation of Fluorescence Navigation During Oncologic Surgery: A Consensus Report. J Nucl Med. 2016:57(1):144-50.

Rowe D E, Carroll R J, Day C L. Prognostic factors for local recurrence, metastasis, and survival rates in squamous-cell carcinoma of the skin, ear, and lip—implications for treatment modality selection. J Am Acad Dermatol. 1992; 26(6):976-90.

Ryu J H, Na J H, Ko H K, You D G, Park S, Jun E, et al. Non-invasive optical imaging of cathepsin B with activatable fluorogenic nanoprobes in various metastatic models. Biomaterials. 2014:35(7):2302-11.

Schaafsma B E, Mieog J S D, Hutteman M, Van der Vorst J R, Kuppen P J K, Lowik C W G M, et al. The Clinical Use of Indocyanine Green as a Near-Infrared Fluorescent Contrast Agent for Image-Guided Oncologic Surgery. J Surg Oncol. 2011; 104(3):323-32.

Sevick-Muraca E M. Translation of near-infrared fluorescence imaging technologies: emerging clinical applications. Annu Rev Med. 2012; 63:217-31.

Sheer D G, Schlom J, Cooper H L. Purification and composition of the human tumor-associated glycoprotein (TAG-72) defined by monoclonal antibodies CC49 and B72.3. Cancer Res. 1988; 48(23):6811-8.

Slavin-Chiorini D C, Horan Hand P H, Kashmiri S V, Calvo B, Zaremba S, Schlom J. Biologic properties of a CH2 domain-deleted recombinant immunoglobulin. Int J Cancer. 1993; 53(1):97-103.

Stewart S L, Wike J M, Kato I, Lewis D R. Michaud F. A population-based study of colorectal cancer histology in the United States, 1998-2001. Cancer. 2006; 107(5 Suppl):1128-41.

Sullivan B, Long D, Alten D, Hitchcock C, Martin E, Magliery T. manuscript in preparation.

Sun D, Bloomston M, Hinkle G. Al-Saif O H, Hall N C, Povoski S P, et al. Radioimmunoguided surgery (RIGS), PET/CT image-guided surgery, and fluorescence image-guided surgery: past, present, and future. Journal of surgical oncology. 2007; 96(4):297-308.

van Dam G M, Themelis G, Crane L M, Harlaar N J, Pleijhuis R G, Kelder W, et al. Intraoperative tumor-specific fluorescence imaging in ovarian cancer by folate receptor-alpha targeting: first in-human results. Nat Med. 2011; 17(10):1315-9.

Yanagihara K, Takigahira M, Tanaka H, Komatsu T, Fukumoto H, Koizumi F, et al. Development and biological analysis of peritoneal metastasis mouse models for human scirrhous stomach cancer. Cancer Sci. 2005; 96(6):323-32.

Yoon S O, Lee T S, Kim S J, Jang M H, Kang Y J, Park J H, et al. Construction, affinity maturation, and biological characterization of an anti-tumor-associated glycoprotein-72 humanized antibody. J Biol Chem. 2006; 281(11): 6985-92.

Zou P, Povoski S P, Hall N C, Carlton M M, Hinkle G H, Xu R X, et al. I-124-HuCC49deltaC(H)2 for TAG-72 antigen-directed positron emission tomography (PET) imaging of LS174T colon adenocarcinoma tumor implants in xenograft mice: preliminary results. World J Surg Oncol. 2010; 8.

Zou P, Xu S, Povoski S P, Wang A, Johnson M A, Martin E W, Jr., et al. Near-infrared fluorescence labeled anti-TAG-72 monoclonal antibodies for tumor imaging in colorectal cancer xenograft mice. Mol Pharm. 2009; 6(2):428-40.

Zou P, Xu S B, Povoski S P, Wang A. Johnson M A, Martin E W, et al. Near-infrared Fluorescence Labeled Anti-TAG-72 Monoclonal Antibodies for Tumor Imaging in Colorectal Cancer Xenograft Mice. Mol Pharm. 2009; 6(2):428-40.

F. Sequences

```
(3E8.scFv) amino acid sequence
                                         SEQ ID NO: 1
MKYLLPTAAAGLLLLAAQPAMAAHHHHHHGSSGGGENLYFQGSSGDI

VMTQSPDSLAVSLGERATINCKSSQSVLYSSNNKNYLAWYQQKPGQP

PKLLIYWASTRESGVPDRFSGSGSGTDFTLTISSLQAEDVAVYYCQQ

YYSYPLTFGGGTKVEIKLSADDAKKDAAKKDDAKKDDAKKDLQVQLV

QSGAEVKKPGASVKVSCKASGYTFTDHAIHWVRQAPGQRLEWMGYFS

PGNDDFKYSQKFQGRVTITADKSASTAYMELSSLRSEDTAVYYCARS

WIMQYWGQGTLVTVSS (3E8.scFv.Cys) amino acid sequence
                                         SEQ ID NO: 2
MKYLLPTAAAGLLLLAAQPAMAAHHHHHHGSSGGGENLYFQGSSGDI

VMTQSPDSLAVSLGERATINCKSSQSVLYSSNNKNYLAWYQQKPGQP

PKLLIYWASTRESGVPDRFSGSGSGTDFTLTISSLQAEDVAVYYCQQ

YYSYPLTFGGGTKVEIKLSADDAKKDAAKKDDAKKDDAKKDLQVQLV

QSGAEVKKPGASVKVSCKASGYTFTDHAIHWVRQAPGQRLEWMGYFS

PGNDDFKYSQKFQGRVTITADKSASTAYMELSSLRSEDTAVYYCARS

WIMQYWGQGTLVTVSSC

SEQ ID NO: 3
MKYLLPTAAAGLLLLAAQPAMA

SEQ ID NO: 4
AHHHHHHGSSGGGENLYFQ

SEQ ID NO: 5
GSSG

SEQ ID NO: 6
LSADDAKKDAAKKDDAKKDDAKKDL (3E8.scFv) nucleotide sequence
                                         SEQ ID NO: 7
CATATGAAATATCTGTTACCTACTGCTGCTGCGGGCCTGCTATTATT

AGCGGCACAACCAGCAATGGCGGCGCATCATCATCATCATCATGGGT

CCTCGGGCGGTGGCGAAAATCTGTATTTTCAGGGTAGCAGCGGCGAT

ATTGTGATGACCCAGAGCCCGGATAGTTTGGCCGTTAGCCTGGGCGA

ACGTGCGACGATTAATTGCAAGAGCAGCCAGAGCGTGCTTTACAGCA

GCAACAATAAGAATTACCTGGCGTGGTATCAGCAAAAACCCGGCCAG

CCGCCGAAACTTTTGATTTATTGGGCGAGCACCCGTGAAAGCGGCGT

GCCGGATCGTTTCTCGGGCTCAGGCAGCGGGACCGATTTTACGCTGA

CCATCAGCAGCCTTCAGGCGGAGGATGTCGCGGTGTACTACTGCCAG

CAGTATTACAGCTATCCGTTGACCTTTGGGGGAGGCACCAAAGTGGA

GATCAAACTGAGCGCGGATGATGCTAAGAAAGATGCGGCGAAGAAGG

ACGATGCGAAAAAGACGACGCAAAAAAGGATCTGCAGGTGCAGCTG

GTGCAGTCGGGTGCGGAAGTGAAGAAACCTGGGGCGTCGGTGAAAGT

GAGCTGCAAAGCGAGCGGCTATACCTTTACCGATCATGCGATTCATT

GGGTGCGTCAAGCGCCAGGCCAGCGTCTGGAATGGATGGGCTATTTT

TCCCCAGGCAACGATGATTTCAAGTATTCCCAGAAGTTCCAAGGGCG
```

CGTGACCATTACCGCCGATAAAAGCGCAAGCACCGCGTATATGGAGC

TGTCCAGCCTGCGTAGCGAAGATACAGCGGTTTACTATTGCGCACGG

AGCTGGATTATGCAATACTGGGGCCAGGGCACCCTGGTGACCGTGAG

CAGCTAAGGATCC (3E8.scFv.Cys) nucleotide sequence

SEQ ID NO: 8

CATATGAAATATCTGTTACCTACTGCTGCTGCGGGCCTGCTATTATT

AGCGGCACAACCAGCAATGGCGGCGCATCATCATCATCATCATGGGT

CCTCGGGCGGTGGCGAAAATCTGTATTTTCAGGGTAGCAGCGGCGAT

ATTGTGATGACCCAGAGCCCGGATAGTTTGGCCGTTAGCCTGGGCGA

ACGTGCGACGATTAATTGCAAGAGCAGCCAGAGCGTGCTTTACAGCA

GCAACAATAAGAATTACCTGGCGTGGTATCAGCAAAAACCCGGCCAG

CCGCCGAAACTTTTGATTTATTGGGCGAGCACCCGTGAAAGCGGCGT

GCCGGATCGTTTCTCGGGCTCAGGCAGCGGGACCGATTTTACGCTGA

CCATCAGCAGCCTTCAGGCGGAGGATGTCGCGGTGTACTACTGCCAG

CAGTATTACAGCTATCCGTTGACCTTTGGGGGAGGCACCAAAGTGGA

GATCAAACTGAGCGCGGATGATGCTAAGAAAGATGCGGCGAAGAAGG

ACGATGCGAAAAAGACGACGCAAAAAAGGATCTGCAGGTGCAGCTG

GTGCAGTCGGGTGCGGAAGTGAAGAAACCTGGGGCGTCGGTGAAAGT

GAGCTGCAAAGCGAGCGGCTATACCTTTACCGATCATGCGATTCATT

GGGTGCGTCAAGCGCCAGGCCAGCGTCTGGAATGGATGGGCTATTTT

TCCCCAGGCAACGATGATTTCAAGTATTCCCAGAAGTTCCAAGGGCG

CGTGACCATTACCGCCGATAAAAGCGCAAGCACCGCGTATATGGAGC

TGTCCAGCCTGCGTAGCGAAGATACAGCGGTTTACTATTGCGCACGG

AGCTGGATTATGCAATACTGGGGCCAGGGCACCCTGGTGACCGTGAG

CAGCTGTTAAGGATCC

SEQ ID NO: 9

MKYLLPTAAAGLLLLAAQPAMAAHHHHHGSSGGGENLYFQGSSGDI

V

3E8.scFv (VH Domain) amino acid sequence

SEQ ID NO: 10

QVQLVQSGAEVKKPGASVKVSCKASGYTFTDHAIHWVRQAPGQRLEW

MGYFSPGNDDFKYSQKFQGRVTITADKSSSTAYMELSSLRSEDTAVY

YCARSWIMQYWGQGTLVTVSS

3E8.scFv (VL Domain) amino acid sequence

SEQ ID NO: 11

DIVMTQSPDSLAVSLGERATINCKSSQSVLYSSNNKNYLAWYQQKPG

QPPKLLIYWASTRESGVPDRFSGSGSGTDFTLTISSLQAEDVAVYYC

QQYYSYPLTFGGGTKVEIK

What is claimed is:

1. A method of performing surgical removal of a tumor in a subject comprising:
   a. administering to a subject intraperitoneally an anti-tumor-associated glycoprotein 72 (TAG-72) imaging agent comprising the formula Y-R, wherein Y comprises an anti-TAG-72 binding moiety and R comprises a first detectable label; wherein the first detectable label "R" comprises any dicyanine dye that emits fluorescent light that is detectable on a clinical optical near infrared fluorescence—(NIRF) imager at above 800 nm; wherein the dicyanin dye is selected from the group consisting of infrared (IR) dye800, AlexaFluor 790, ZW-800, Indocyanine Green, and S0456; wherein the anti-TAG-72 binding moiety comprises 3E8.scFv; and
   b. guiding the surgical removal of the tumor using optical surgical navigation wherein the combination of the 3E8.scFv and the detectable label causes the signaling intensity of the anti-tumor-associated glycoprotein 72 (TAG-72) imaging agent in the liver and tumor tissue to differ.

2. The method of claim 1, wherein the method further comprises assaying the tumor using the anti-TAG-72 imaging agent to determine the possibility of surgical removal after step a and prior to step b.

3. The method of claim 1, wherein the method further comprises monitoring the progress of the surgical removal.

4. The method of claim 1, wherein the anti-TAG-imaging agent comprises a second detectable label and wherein the second label is a radiolabel.

5. A method of making ®-anti-TAG-72 imaging agent comprising the formula Y R, wherein Y comprises an anti-TAG-72 binding moiety and R comprises a first detectable label; wherein the first detectable label "R" comprises any dicyanine dye that emits fluorescent light that is detectable on a clinical optical near infrared fluorescence (NIRF) imager at primarily above 800 nm; wherein the dicyanine dye is selected from the group consisting of IRDYER800, AlexaFluor 790, ZW-800, Indocyanine Green, and S0456; and wherein ® is a radioactive labeling atom detectable by single photon emission computerized tomography (SPECT)/computed tomography (CT), or positron emission tomography (PET)/CT, radioguided antigen-directed surgery (RADS), surgical guidance, or a both SPECT/CT or PET/CT and RADS said method comprising
   a. providing an anti-TAG-72 imaging agent comprising a tyrosine residue; and
   b. reacting the biomolecule with a chloramine and an iodine source under conditions effective to form an iodinated biomolecule, wherein the iodinated biomolecule comprises an iodinated tyrosine residue.

* * * * *